(12) United States Patent
Khalifah

(10) Patent No.: US 12,139,472 B2
(45) Date of Patent: Nov. 12, 2024

(54) INHIBITORS OF ADVANCED GLYCATION END PRODUCTS

(71) Applicant: PRAETEGO INC, Durham, NC (US)

(72) Inventor: Raja G. Khalifah, Raleigh, NC (US)

(73) Assignee: Praetego Inc, Durham, NC (US)

( * ) Notice: Subject to any disclaimer, the term of this patent is extended or adjusted under 35 U.S.C. 154(b) by 794 days.

(21) Appl. No.: 17/164,817

(22) Filed: Feb. 1, 2021

(65) Prior Publication Data

US 2021/0163450 A1 Jun. 3, 2021

Related U.S. Application Data

(63) Continuation-in-part of application No. PCT/US2020/044611, filed on Jul. 31, 2020.

(60) Provisional application No. 63/006,706, filed on Apr. 7, 2020, provisional application No. 62/881,607, filed on Aug. 1, 2019.

(51) Int. Cl.
| | | |
|---|---|---|
| *C07D 401/14* | (2006.01) | |
| *C07D 213/38* | (2006.01) | |
| *C07D 233/64* | (2006.01) | |
| *C07D 401/04* | (2006.01) | |

(52) U.S. Cl.
CPC ......... *C07D 401/14* (2013.01); *C07D 213/38* (2013.01); *C07D 233/64* (2013.01); *C07D 401/04* (2013.01)

(58) Field of Classification Search
CPC ............... C07D 401/14; C07D 213/38; C07D 233/64
See application file for complete search history.

(56) References Cited

U.S. PATENT DOCUMENTS 9,428,533 B2 * 8/2016 Khalifah ................. A61P 19/04

FOREIGN PATENT DOCUMENTS

| WO | 2004/019889 A2 | 3/2004 |
| WO | 2008/013660 A2 | 1/2008 |

OTHER PUBLICATIONS

S M Berge. Pharmaceutical Salts. Journal of Pharmaceutical Sciences. Jan. 1977 vol. 66 No. 1. p. 1-19 (Year: 1977).*
Martin Busch et al. The Advanced Glycation End Product N-Carboxymethyllysine Is Not a Predictor of Cardiovascular Events and Renal Outcomes in Patients With Type 2 Diabetic Kidney Disease and Hypertension. American Journal of Kidney Diseases, vol. 48, No. 4 Oct. 2006: pp. 571-579. (Year: 2006).*
Richard D. Semba et al. Dietary Intake of Advanced Glycation End Products Did Not Affect Endothelial Function and Inflammation in Healthy Adults in a Randomized Controlled Trial. The Journal of Nutrition. Apr. 17, 2014; doi:10.3945/jn.113.189480. 1037-1042. (Year: 2014).*
S M Bronner. Design of a brain-penetrant CDK4/6 inhibitor for glioblastoma. Bioorganic & Medicinal Chemistry Letters. 29 (2019) 2294-2301. (Year: 2019).*
Udit Agrawal and Vivek Tiwari. Fibrodysplasia Ossificans Progressiva. NCBI Bookshelf. A service of the National Library of Medicine, National Institutes of Health. StatPearls [Internet]. Treasure Island (FL): StatPearls Publishing; Jan. 2023. pp. 1-7 (Year: 2023).*
International Search Report and Written Opinion for PCT/US2020/044611, mailed Oct. 19, 2020.
Audie, et al., "New 2,3-diaminopropionic acid inhibitors of AGE and ALE formation", Organic & Biomolecular Chemistry, vol. 11, No. 5, Jan. 1, 2013 (Jan. 1, 2013 ), pp. 773-780.
Khalifah, et al., "Post-Amadori AGE Inhibition as a Therapeutic Target for Diabetic Complications: A Rational Approach to Second-Generation Amadorin Design", Annals of the New York Academy of Sciences, vol. 1043, No. 1, Jun. 1, 2005 (Jun. 1, 2005 ), pp. 793-806.
Lohou, et al., "Multifunctional diamine AGE/ALE inhibitors with potential therapeutical properties against Alzheimer's disease", European Journal of Medicinal Chemistry, vol. 122, Apr. 30, 2016 (Apr. 30, 2016), pp. 702-722.

* cited by examiner

*Primary Examiner* — Kortney L. Klinkel
*Assistant Examiner* — Richard Grant Peckham
(74) *Attorney, Agent, or Firm* — Wilson Sonsini Goodrich & Rosati

(57) ABSTRACT

The present disclosure provides compounds of the formula

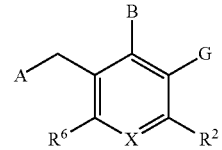

pharmaceutical compositions, and methods for treating or inhibiting development of AGE- and/or ALE-associated complications in subjects in need thereof.

21 Claims, No Drawings

INHIBITORS OF ADVANCED GLYCATION END PRODUCTS

CROSS-REFERENCE TO RELATED APPLICATIONS

This application is a continuation-in-part of International Application No. PCT/US2020/044611, filed Jul. 31, 2020, which claims the benefit of priority of U.S. Provisional Patent Application No. 62/881,607, filed Aug. 1, 2019, and U.S. Provisional Patent Application No. 63/006,706, filed Apr. 7, 2020, each of which is incorporated by reference in its entirety.

STATEMENT REGARDING FEDERALLY SPONSORED RESEARCH

This invention was made with government support under R43DK120063 and R42DK120063 awarded by the National Institutes of Health. The government has certain rights in the invention.

BACKGROUND OF DISCLOSURE

Field of the Disclosure

This application relates to the fields of chemistry, medicine, renal disease, vascular disease, hyperlipidemia, hyperglycemia, advanced glycation end-products, complications of diabetes and advanced lipoxidation end-products.

Technical Background

Advanced glycation end-products (AGEs) are carbohydrate-derived chemical modifications and crosslinks that accumulate in long-lived tissue proteins during normal aging. The increased rate of accumulation of AGEs during hyperglycemia is implicated in the development of long-term complications of diabetes, including but not limited to retinopathy, nephropathy, neuropathy, atherosclerosis, and cardiovascular disease. In addition, AGE formation has been implicated in a number of other pathologies, such as normal aging processes, arthritis, connective tissue disease, amyloidoses, and neurodegenerative amyloid diseases, such as Alzheimer's.

Advanced lipoxidation end products (ALEs) are lipid-derived chemical modifications and crosslinks that also accumulate in long-lived tissue proteins during normal aging, and are associated with hyperlipidemia, vascular disease, and renal disease in both diabetic and non-diabetic animal models. It is now recognized that some compounds, such as $N^\varepsilon$-(carboxymethyl) lysine (CMIL) and $N^\varepsilon$-(carboxyethyl)lysine (CEL), may be derived from either carbohydrates or lipids, leading to their designation as AGE/ALEs. Other compounds, such as pentosidine, appear to be true AGEs, while other compounds, such as malondialdehyde-lysine (MDA-Lys) and hydroxynonenal-lysine (HNE-Lys), are acknowledged to be ALEs, derived exclusively from lipids.

The elucidation of the pathogenic mechanisms of AGE and ALE-associated complications associated with hyperglycemia and/or hyperlipidemia is critical for developing rational therapy for their treatment and prevention. However, there is no consensus at present on the relative importance of the different possible pathogenic mechanisms that potentially contribute to these diabetic complications.

The compound pyridoxamine has recently been shown to inhibit both AGE and ALE formation in vitro, and to be useful for treating and preventing AGE and ALE-associated complications in hyperglycemic, hyperlipidemic, and hyperglycemic-hyperlipidemic animal models. (See, for example, U.S. Pat. No. 5,985,857; WO 00/21516; WO 00/23063) Such complications include, but are not limited to, diabetic nephropathy, proteinuria, impaired glomerular clearance, retinopathy, neuropathy, atherosclerosis, diabetes-associated hyperlipidemia, oxidative modification of proteins, obesity-related complications, proliferation or smooth muscle cells in the aorta, coronary artery occlusion, and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient.

However, there remains a need in the art for further options to treat or inhibit development of AGE- and ALE-associated complications in patients in need thereof, particularly patients with hyperglycemia and/or hyperlipidemia.

SUMMARY OF THE DISCLOSURE

The present disclosure provides compounds, pharmaceutical compositions, and methods for treating or inhibiting development of AGE- and/or ALE-associated complications in a subject in need thereof.

Thus, in one aspect the disclosure provides novel compounds as described herein, and pharmaceutical compositions thereof. In a preferred embodiment, the methods comprise administering one or more of the compounds or pharmaceutical compositions of the disclosure to subjects suffering from hyperglycemia and/or hyperlipidemia.

In another aspect, the disclosure further provides methods of treating or inhibiting development of disorders, including diabetic nephropathy, proteinuria, impaired glomerular clearance, retinopathy, neuropathy, atherosclerosis, diabetes-associated hyperlipidemia, oxidative modification of proteins, arthritis, connective tissue diseases, amyloidosis, obesity-related complications, proliferation of smooth muscle cells in the aorta, coronary artery occlusion, and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient. Said methods comprise administering an effective amount of one or more compounds of the present disclosure as described herein, or a pharmaceutically acceptable salt thereof, to a subject in need of such treatment.

DETAILED DESCRIPTION OF THE DISCLOSURE

In a first aspect, the disclosure provides the compound of formula (I),

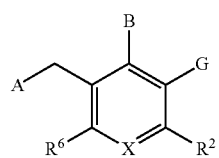

or a pharmaceutically acceptable salt thereof, wherein
X is N, N—O or CR$^1$;
G is —OH, —SH, —NH$_2$, or —N(R$^G$)$_2$, wherein R$^G$ is hydrogen, (C$_1$-C$_6$)alkyl or —C(O)(C$_1$-C$_6$)alkyl;
A is

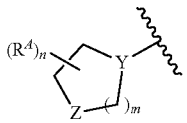

wherein
Y is N;
Z is CH$_2$, C(H)R$^A$, C(R$^A$)$_2$, O, or NR$^A$;
m is 0, 1, 2, or 3;
provided that
when m is 0, Z is CH$_2$, C(H)R$^A$ or C(R$^A$)$_2$, and when m is 2, Z is O;
R$^A$ is (C$_1$-C$_6$)alkyl, halogen, —OR$^{A1}$, —N(R$^{A1}$)$_2$, —SR$^{A1}$, —S(O)R$^{A1}$, —S(O)$_2$R$^{A1}$, —COOR$^{A1}$, —CON(R$^{A1}$)$_2$ or —(C$_1$-C$_6$)alkyl-OR$^{A1}$
wherein R$^{A1}$ is hydrogen, (C$_1$-C$_6$)alkyl, or —C(O)(C$_1$-C$_6$)alkyl, or two R$^{A1}$ together with N-atom to which they are attached form a morpholinyl; and
n is 0, 1, 2, 3, 4, 5 or 6;
B is of the formula,

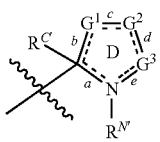

wherein
ring D is (i) monocyclic, and
(ii) unsaturated or aromatic;
R$^{C'}$ is hydrogen;
G$^1$ is O, S, N or NR$^{N'}$;
G$^2$ and G$^3$ each are independently N, O, CR$^3$, C(R$^3$)$_2$ or NR$^{N'}$, wherein each R$^3$ is independently -Z$^3$-M-Z$^4$-R$^Z$, wherein M is —C(O)—, —C(S)—, —S(O)—, —S(O)$_2$—, or absent,
Z$^3$ and Z$^4$ are independently —O—, —S—, —N(R$^{N3}$)— or absent, wherein
R$^{N3}$ is hydrogen, (C$_1$-C$_6$)alkyl, (C$_2$-C$_6$)alkenyl, (C$_1$-C$_6$)alkynyl, (C$_1$-C$_6$)haloalkyl, (C$_1$-C$_6$)alkanoyl, (C$_3$-C$_8$)cycloalkanoyl, heterocycloyl, aroyl, heteroaroyl, (C$_1$-C$_6$)alkoxycarbonyl or aryl(C$_1$-C$_6$)alkoxycarbonyl, wherein R$^{N3}$ is optionally substituted with one or more groups which are independently halogen, —OH, amino, (C$_1$-C$_6$)alkylamino, (C$_1$-C$_6$)dialkylamino, —NO$_2$, —CN, (C$_1$-C$_6$)alkyl, aryl, heterocyclyl, heteroaryl, (C$_3$-C$_8$)cycloalkyl, (C$_1$-C$_6$)haloalkyl, (C$_1$-C$_6$)alkoxy, (C$_1$-C$_6$)alkanoyl or aroyl;
R$^Z$ is —H, —(C$_1$-C$_6$)alkyl, —(C$_2$-C$_6$)alkenyl, —(C$_1$-C$_6$)alkynyl, or —(C$_1$-C$_6$)haloalkyl, —(C$_3$-C$_8$)cycloalkyl, —(C$_1$-C$_6$)alkylaryl, -heterocycle, -aryl, or -heteroaryl, wherein
R$^Z$ is optionally substituted with at least one R$^{Z'}$, wherein each R$^{Z'}$ is independently -halogen, —OR, —(C$_1$-C$_6$)alkoxy, —C(O)OR, —C(O)R, —C(O)NR$_2$, —S(O)$_2$R, —OS(O)$_2$R, -cyano, -nitro, —(C$_1$-C$_6$)alkyl, —(C$_1$-C$_6$)haloalkyl, —(C$_3$-C$_8$)cycloalkyl, -heterocycloalkyl, or heteroaryl,
provided when M is —S(O)—, —S(O)$_2$— or absent, at least one of Z$^3$ and Z$^4$ is also absent;
or two R$^3$ taken together are oxo;
R$^{N'}$ is hydrogen or C$_1$-C$_6$alkyl;
bonds a, b, c, d, and e are independently a single or double bond, provided that
(i) no two consecutive atoms in ring D are both oxygen;
(ii) no two consecutive bonds are both double bonds;
(iii) if a or b is a double bond, then R$^{C'}$ is absent; and
(iv) if a or e is a double bond, then R$^{N'}$ is absent;
(v) if b or c is a double bond, then G$^1$ is not O or S;
(vi) if c or d is a double bond, then G$^2$ is not 0;
(vii) if d or e is a double bond, then G$^3$ is not 0;
R$^1$, R$^2$, and R$^6$ are independently hydrogen, halogen, —NO$_2$, —CN or R$^C$, provided that when X=CR$^1$,
(i) R$^2$, R$^6$, and R$^{N1}$ are not phenyl;
(ii) R$^C$ is not aryl, heteroaryl, heterocyclyl or (C$_2$-C$_6$)alkenyl
(iii) and G$^1$=N together, then G$_2$ is not O; and
(iv) two R$^C$ together may not form oxo;
and provided that when X=N, and
(i) G$^1$ is N, G$^3$ is CR$^3$ and G$^2$ is N, and bonds b and d are each a double bond, all simultaneously; or
(ii) G$^1$ is N, G$^3$ is C(O), G$^2$ is NR$^{N'}$, and bond b is a double bond, all simultaneously;
either R$^2$ or R$^6$ is not —NH-aryl or —NH-heteroaryl,
or a pharmaceutically acceptable salt thereof.
In certain embodiments, the compounds of formula (I) are wherein
Z is CH$_2$, C(H)R$^A$, C(R$^A$)$_2$, or O;
m is 0 or 2;
provided that
when m is 0, Z is CH$_2$, C(H)R$^A$ or C(R$^A$)$_2$, and when m is 2, Z is O.
In another embodiment, the disclosure provides compounds of formula (I) wherein X is N and G is hydrogen.
In another embodiment, the disclosure provides compounds of formula (I) wherein
B is aromatic;
G$^1$ is O, S, N or NR$^{N'}$; and
G$^2$ and G$^3$ are each independently O, N or CR$^3$.
In another embodiment, the disclosure provides compounds of formula (I) wherein B is imidazolyl, oxazolyl, pyrazolyl, pyrrolyl or isoxazolyl wherein each carbon atom is substituted by R$^3$.
In another embodiment, the disclosure provides compounds of formula (I) wherein B is imidazolyl wherein each carbon atom is substituted by R$^3$.
In another embodiment, the disclosure provides compounds of formula (I) wherein each R$^3$ is independently R$^{Z3}$, wherein
R$^{Z3}$ is hydrogen, (C$_1$-C$_6$)alkyl, (C$_1$-C$_6$)haloalkyl, (C$_3$-C$_8$) cycloalkyl, (C$_1$-C$_6$)alkylaryl, heterocyclyl, aryl or heteroaryl, wherein R$^{Z3}$ is optionally substituted with at least one R$^{Z3'}$, wherein
each R$^{Z3'}$ is independently halogen, cyano, —OR, —C(O)OR, —C(O)R, —C(O)NR$_2$, (C$_1$-C$_6$)alkyl, (C$_1$-C$_6$)haloalkyl, (C$_3$-C$_8$)cycloalkyl or heterocycloalkyl, wherein each R is independently hydrogen, (C$_1$-C$_6$)alkyl or (C$_1$-C$_6$)haloalkyl.

In another embodiment, the disclosure provides compounds of formula (I) wherein
$R^2$ and $R^6$ are each hydrogen, halogen, —$NO_2$, —CN or $R^{Z6}$ wherein
$R^{Z6}$ is ($C_1$-$C_6$)alkyl, ($C_1$-$C_6$)haloalkyl, ($C_3$-$C_8$)cycloalkyl, ($C_1$-$C_6$)alkylaryl, heterocyclyl, aryl or heteroaryl, wherein $R^{Z6}$ is optionally substituted with at least one $R^{Z6'}$,
wherein each $R^{Z6'}$ is independently halogen, —OR, —C(O)OR, —C(O)R, ($C_1$-$C_6$)alkyl or ($C_1$-$C_6$)haloalkyl, wherein each R is independently hydrogen, ($C_1$-$C_6$)alkyl or ($C_1$-$C_6$)haloalkyl.

In another embodiment, the disclosure provides compounds of formula (I) wherein
$R^{N'}$ is hydrogen, ($C_1$-$C_6$)alkyl, ($C_1$-$C_6$)haloalkyl, ($C_1$-$C_6$)alkanoyl, ($C_3$-$C_8$)cycloalkyl, aryl, heteroaryl, ($C_3$-$C_8$)cycloalkanoyl, heterocycloyl, aroyl, heteroaroyl, ($C_1$-$C_6$)alkoxycarbonyl or aryl($C_1$-$C_6$)alkoxycarbonyl, wherein
$R^{N'}$ is optionally substituted with one or more groups which are independently halogen, —$OR^{N''}$, —$NR^{N''}_2$, —$NO_2$, —CN, ($C_1$-$C_6$)alkyl, aryl, heterocyclyl, heteroaryl, ($C_3$-$C_8$)cycloalkyl or ($C_1$-$C_6$)haloalkyl,
wherein each $R^{N''}$ is independently hydrogen, ($C_1$-$C_6$)alkyl, ($C_1$-$C_6$)haloalkyl, ($C_1$-$C_6$)alkoxy, ($C_3$-$C_8$)cycloalkyl, heterocycloalkyl, aryl or heteroaryl.

In another embodiment, the disclosure provides compounds of formula (I) wherein A is

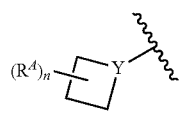

wherein n is 0, 1, 2 or 3.

In another embodiment, the disclosure provides compounds of formula (I) wherein A is

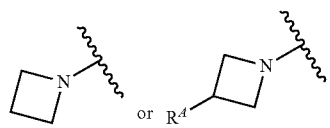

In another embodiment, the disclosure provides compounds of formula (I) wherein A is

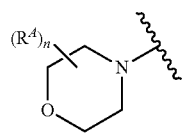

In another embodiment, the disclosure provides compounds of formula (I) wherein $R^4$ is ($C_1$-$C_6$)alkyl, halogen or —($C_1$-$C_6$)alkyl-$OR^{41}$, wherein $R^{41}$ is hydrogen or ($C_1$-$C_6$)alkyl.

In another embodiment, the disclosure provides compounds of formula (I) wherein $R^4$ is ($C_1$-$C_6$)alkyl, halogen, ($C_1$-$C_6$)alkyl-$OR^{41}$, or —$COOR^{41}$, wherein $R^{41}$ is hydrogen or ($C_1$-$C_6$)alkyl, or two $R^{41}$ together with N-atom to which they are attached form a morpholinyl.

In another embodiment, the disclosure provides compounds of formula (I) wherein B is not aromatic and $G^1$, $G^2$, and $G^3$ are each independently O, N, $CR^3$, $C(R^3)_2$ or $N(R^{N'})$.

In another embodiment, the disclosure provides compounds of formula (I) wherein
B is pyrrolidinyl, pyrazolidinyl, imidazolidinyl, isoxazolidinyl, oxazolidinyl, triazolidinyl or tetrazolidinyl, wherein each carbon is substituted by two $R^3$ and each nitrogen is substituted by $R^{N'}$.

In another embodiment, the disclosure provides compounds of formula (I) wherein
each $R^3$ is independently $R^{Z3}$, wherein
$R^{Z3}$ is hydrogen, ($C_1$-$C_6$)alkyl, ($C_1$-$C_6$)haloalkyl, ($C_3$-$C_8$)cycloalkyl, ($C_1$-$C_6$)alkylaryl, heterocyclyl, aryl or heteroaryl, wherein $R^{Z3}$ is optionally substituted with at least one $R^{Z3'}$, wherein
each $R^{Z3'}$ is independently -halogen, -cyano, —OR, —C(O)OR, —C(O)R, —C(O)$NR_2$, ($C_1$-$C_6$)alkyl, ($C_1$-$C_6$)haloalkyl, ($C_3$-$C_8$)cycloalkyl or heterocycloalkyl.

In another embodiment, the disclosure provides compounds of formula (I) wherein
$R^2$ and $R^6$ are each hydrogen, halogen, —$NO_2$, —CN or —$R^{Z6}$ wherein
$R^{Z6}$ is ($C_1$-$C_6$)alkyl, ($C_1$-$C_6$)haloalkyl, ($C_3$-$C_8$)cycloalkyl, ($C_1$-$C_6$)alkylaryl, heterocyclyl, aryl or heteroaryl, wherein $R^{Z6}$ is optionally substituted with at least one $R^{Z6'}$,
wherein each $R^{Z6'}$ is independently halogen, —OR, —C(O)OR, —C(O)R, ($C_1$-$C_6$)alkyl or ($C_1$-$C_6$)haloalkyl, wherein $R^{Z6'}$ is optionally substituted with one or more R'.

In another embodiment, the disclosure provides compounds of formula (I) wherein
each $R^{N'}$ is hydrogen, ($C_1$-$C_6$)alkyl, ($C_1$-$C_6$)haloalkyl, ($C_1$-$C_6$)alkanoyl, ($C_3$-$C_8$)cycloalkyl, aryl, heteroaryl, ($C_3$-$C_8$)cycloalkanoyl, heterocycloyl, aroyl, heteroaroyl, ($C_1$-$C_6$)alkoxycarbonyl or aryl($C_1$-$C_6$)alkoxycarbonyl, wherein
$R^{N'}$ is optionally substituted with one or more groups which are independently halogen, —$OR^{N''}$, —$NR^{N''}_2$, —$NO_2$, —CN, ($C_1$-$C_6$)alkyl, aryl, heterocyclyl, heteroaryl, ($C_3$-$C_8$)cycloalkyl or —($C_1$-$C_6$)haloalkyl,
wherein each $R^{N''}$ is independently hydrogen, ($C_1$-$C_6$)alkyl, ($C_1$-$C_6$)haloalkyl, ($C_1$-$C_6$)alkoxy, ($C_3$-$C_8$)cycloalkyl, heterocycloalkyl, aryl or heteroaryl, wherein the alkyl and alkoxy are optionally substituted with one or more R'.

In another embodiment, the disclosure provides compounds of formula (I) wherein X is $CR^1$ and G is hydrogen.

In another embodiment, the disclosure provides compounds of formula (I) wherein
$R^1$ is —CN, —$NO_2$, halogen, —C(O)$OR^4$, —C(O)$R^4$, —C(O)N($R^4$)$_2$, —S(O)$R^4$, —S(O)$_2R^4$ or —S(O)$_2$N($R^4$)$_2$, wherein
each $R^4$ is independently hydrogen, ($C_1$-$C_6$)alkyl, ($C_2$-$C_6$)alkenyl, ($C_3$-$C_8$)cycloalkyl, ($C_1$-$C_6$)alkylaryl, heterocyclyl, aryl or heteroaryl, wherein
$R^4$ is optionally substituted with at least one group, each of which are independently halogen, —OH, ($C_1$-$C_6$)alkoxy, —C(O)$R^{41}$, —S(O)$_2R^{41}$, —OS(O)$_2R^{41}$, —CN, —$NO_2$, ($C_1$-$C_6$)alkyl or ($C_1$-$C_6$)haloalkyl, wherein $R^{41}$ is hydrogen, $(C_1-C_6)$alkyl, $(C_1-C_6)$haloalkyl, $(C_1-C_6)$alkoxy, $(C_3-C_8)$cycloalkyl, heterocycloalkyl, aryl or heteroaryl.

In another embodiment, the disclosure provides compounds of formula (I) wherein
B is aromatic; and
$G^1$ is O, S, N or $NR^{N'}$; and
$G^2$ and $G^3$ are each independently O, N or $CR^3$.

In another embodiment, the disclosure provides compounds of formula (I) wherein B is imidazolyl, oxazolyl, pyrazolyl, pyrrolyl or isoxazolyl wherein each carbon atom is substituted by $R^3$.

In another embodiment, the disclosure provides compounds of formula (I) wherein B is imidazolyl wherein each carbon atom is substituted by $R^3$.

In another embodiment, the disclosure provides compounds of formula (I) wherein each
$R^3$ is independently $R^{Z3}$, wherein
$R^{Z3}$ is hydrogen, $(C_1-C_6)$alkyl, $(C_1-C_6)$haloalkyl, $(C_3-C_8)$cycloalkyl, $(C_1-C_6)$alkylaryl, heterocyclyl, aryl or heteroaryl, wherein $R^{Z3}$ is optionally substituted with at least one $R^{Z3'}$, wherein
each $R^{Z3'}$ is independently halogen, —CN, —OR, —C(O)OR, —C(O)R, —C(O)NR_2, $(C_1-C_6)$alkyl, $(C_1-C_6)$haloalkyl, $(C_3-C_8)$cycloalkyl or heterocycloalkyl.

In another embodiment, the disclosure provides compounds of formula (I) wherein
$R^2$ and $R^6$ are each hydrogen, halogen, —NO_2, —CN or —$R^{Z6}$ wherein
$R^{Z6}$ is $(C_1-C_6)$alkyl, $(C_1-C_6)$haloalkyl, $(C_3-C_8)$cycloalkyl, $(C_1-C_6)$alkylaryl, heterocyclyl, aryl or heteroaryl, wherein $R^{Z6}$ is optionally substituted with at least one $R^{Z6'}$
wherein each $R^{Z6'}$ is independently halogen, —OR, —C(O)OR, —C(O)R, $(C_1-C_6)$alkyl or $(C_1-C_6)$haloalkyl, wherein $R^{Z6'}$ is optionally substituted with one or more R'.

In another embodiment, the disclosure provides compounds of formula (I) wherein
$R^{N'}$ is hydrogen, $(C_1-C_6)$alkyl, $(C_1-C_6)$haloalkyl, $(C_1-C_6)$alkanoyl, $(C_3-C_8)$cycloalkyl, aryl, heteroaryl, $(C_3-C_8)$cycloalkanoyl, heterocycloyl, aroyl, heteroaroyl, $(C_1-C_6)$alkoxycarbonyl or aryl$(C_1-C_6)$alkoxycarbonyl, wherein
$R^{N'}$ is optionally substituted with one or more groups which are independently halogen, —$OR^{N''}$, —$NR^{N''}_2$, —NO_2, —CN, $(C_1-C_6)$alkyl, aryl, heterocyclyl, heteroaryl, $(C_3-C_8)$cycloalkyl or $(C_1-C_6)$haloalkyl,
wherein each $R^{N''}$ is independently hydrogen, $(C_1-C_6)$alkyl, $(C_1-C_6)$haloalkyl, $(C_1-C_6)$alkoxy, $(C_3-C_8)$cycloalkyl, heterocycloalkyl, aryl or heteroaryl, wherein the alkyl and alkoxy are optionally substituted with one or more R'.

In another embodiment, the disclosure provides compounds of formula (I) wherein B is not aromatic and $G^1$, $G^2$, and $G^3$ are each independently O, N, $CR^3$, $C(R^3)_2$ or $N(R^{N'})$.

In another embodiment, the disclosure provides compounds of formula (I) wherein B is pyrrolidinyl, pyrazolidinyl, imidazolidinyl, isoxazolidinyl, oxazolidinyl, triazolidinyl or tetrazolidinyl, wherein each carbon is substituted by two $R^3$ and each nitrogen is substituted by $R^{N'}$.

In another embodiment, the disclosure provides compounds of formula (I) wherein
each $R^3$ is independently $R^{Z3}$, wherein
$R^{Z3}$ is hydrogen, $(C_1-C_6)$alkyl, $(C_1-C_6)$haloalkyl, $(C_3-C_8)$cycloalkyl, $(C_1-C_6)$alkylaryl, heterocyclyl, aryl or heteroaryl, wherein $R^{Z3}$ is optionally substituted with at least one $R^{Z3'}$, wherein
each $R^{Z3'}$ is independently halogen, —CN, —OR, —C(O)OR, —C(O)R, —C(O)NR_2, $(C_1-C_6)$alkyl, $(C_1-C_6)$haloalkyl, $(C_3-C_8)$cycloalkyl or heterocycloalkyl.

In another embodiment, the disclosure provides compounds of formula (I) wherein
$R^2$ and $R^6$ are each hydrogen, halogen, —NO_2, —CN or —$R^{Z6}$ wherein
$R^{Z6}$ is $(C_1-C_6)$alkyl, $(C_1-C_6)$haloalkyl, $(C_3-C_8)$cycloalkyl, $(C_1-C_6)$alkylaryl, heterocyclyl, aryl or heteroaryl, wherein $R^{Z6}$ is optionally substituted with at least one $R^{Z6'}$
wherein each $R^{Z6'}$ is independently halogen, —OR, —C(O)OR, —C(O)R, $(C_1-C_6)$alkyl or $(C_1-C_6)$haloalkyl, wherein $R^{Z6'}$ is optionally substituted with one or more R'.

In another embodiment, the disclosure provides compounds of formula (I) wherein
each $R^{N'}$ is independently hydrogen, $(C_1-C_6)$alkyl, $(C_1-C_6)$haloalkyl, $(C_1-C_6)$alkanoyl, $(C_3-C_8)$cycloalkyl, aryl, heteroaryl, $(C_3-C_8)$cycloalkanoyl, heterocycloyl, aroyl, heteroaroyl, $(C_1-C_6)$alkoxycarbonyl or aryl$(C_1-C_6)$alkoxycarbonyl, wherein
$R^{N'}$ is optionally substituted with one or more groups which are independently halogen, —$OR^{N''}$, —$NR^{N''}_2$, —NO_2, —CN, $(C_1-C_6)$alkyl, aryl, heterocyclyl, heteroaryl, $(C_3-C_8)$cycloalkyl or $(C_1-C_6)$haloalkyl,
wherein each $R^{N''}$ is independently hydrogen, $(C_1-C_6)$alkyl, $(C_1-C_6)$haloalkyl, $(C_1-C_6)$alkoxy, $(C_3-C_8)$cycloalkyl, heterocycloalkyl, aryl or heteroaryl, wherein the alkyl and alkoxy are optionally substituted with one or more R'.

In another embodiment, the disclosure provides compounds of formula (I) wherein the compound of formula (I) is

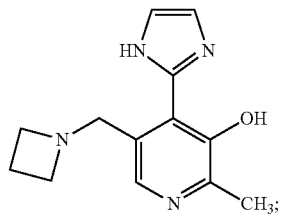

5-(azetidin-1-yl-methyl)-4-(1H-imidazol-2-yl)-2-methylpyridin-3-ol

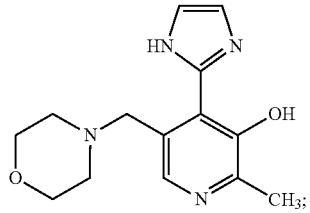

4-(1H-imidazol-2-yl)-2-methyl-5-(morpholinomethyl)pyridin-3-ol

-continued

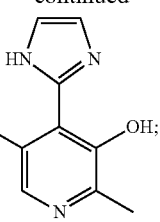

4-(1H-imidazol-2-yl)-2-methyl-5-((4-methylpiperazin-1-yl)methyl)pyridin-3-ol

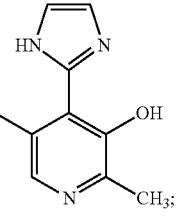

1-((5-hydroxy-4-(1H-imidazol-2-yl)-6-methylpyridin-3-yl)methyl)azetidine-3-carboxylic acid

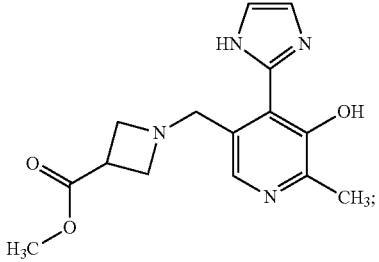

methyl 1-((5-hydroxy-4-(1H-imidazol-2-yl)-6-methylpyridin-3-yl)methyl)azetidine-3-carboxylate

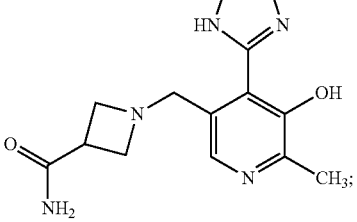

1-((5-hydroxy-4-(1H-imidazol-2-yl)-6-methylpyridin-3-yl)methyl)azetidine-3-carboxamide

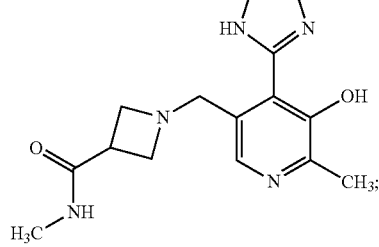

1-((5-hydroxy-4-(1H-imidazol-2-yl)-6-methylpyridin-3-yl)methyl)-N-methylazetidine-3-carboxamide -continued

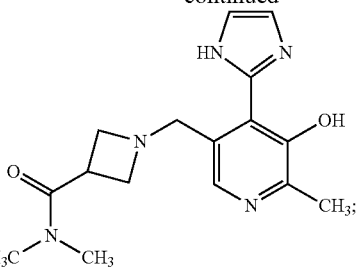

1-((5-hydroxy-4-(1H-imidazol-2-yl)-6-methylpyridin-3-yl)methyl)-N,N-dimethylazetidine-3-carboxamide

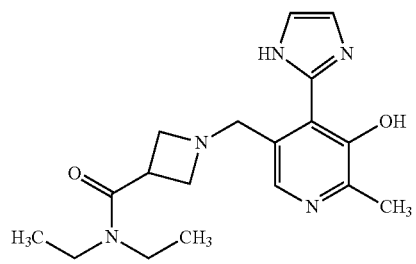

N,N-diethyl-1-((5-hydroxy-4-(1H-imidazol-2-yl)-6-methylpyridin-3-yl)methyl)azetidine-3-carboxamide

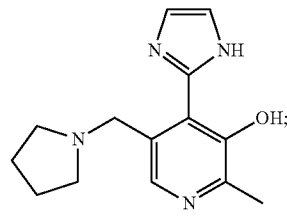

4-(1H-imidazol-2-yl)-2-methyl-5-(pyrrolidin-1-ylmethyl)pyridin-3-ol

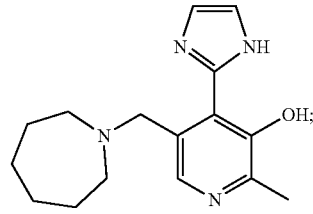

5-(azepan-1-ylmethyl)-4-(1H-imidazol-2-yl)-2-methylpyridin-3-ol

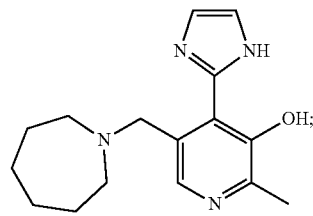

5-(azepan-1-ylmethyl)-4-(1H-imidazol-2-yl)pyridin-3-ol

-continued

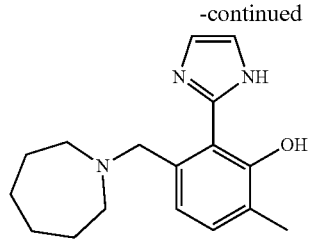

3-(azepan-1-ylmethyl)-2-(1H-imidazol-
2-yl)-6-methylphenol

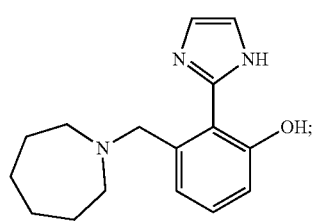

3-(azepan-1-ylmethyl)-2-(1H-imidazol-
2-yl)phenol

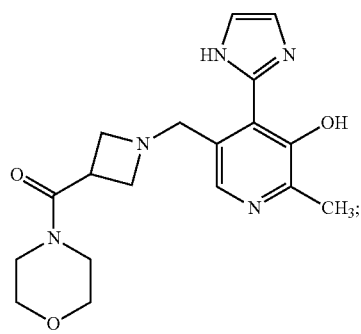

(1-((5-hydroxy-4-(1H-imidazol-2-yl)-6-
methylpyridin-3-yl)methyl)azetidin-3-yl)
(morpholino)methanone

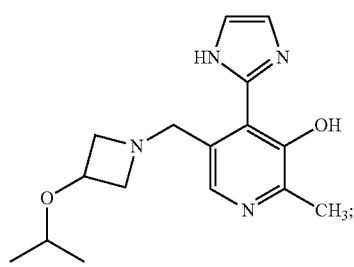

4-(1H-imidazol-2-yl)-5-((3-
isopropoxyazetidin-1-yl)methyl)-2-
methylpyridin-3-ol or a pharmaceutically acceptable salt thereof.

In another aspect, the disclosure provides compounds that are:

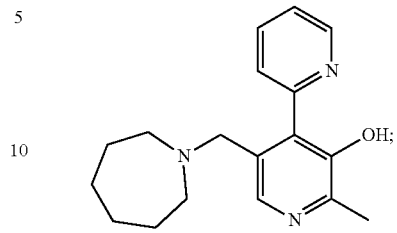

5'-(azepan-1-ylmethyl)-2'-
methyl-[2,4'-bipyridin]-3'-ol;

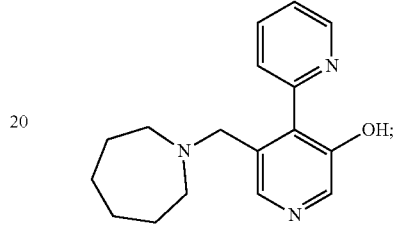

5'-(azepan-1-ylmethyl)-
[2,4'-bipyridin]-3'-ol

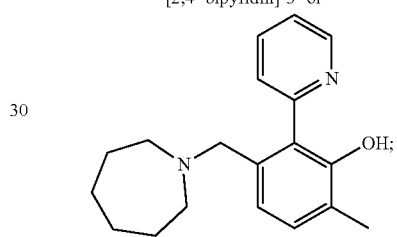

3-(azepan-1-ylmethyl)-6-
methyl-2-(pyridin-2-yl)phenol

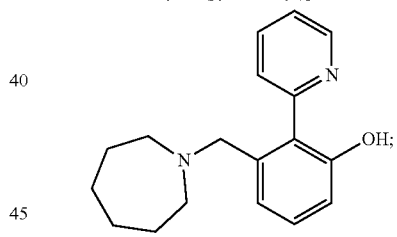

3-(azepan-1-ylmethyl)-
2-(pyridin-2-yl)phenol;

or a pharmaceutically acceptable salt thereof.

In another aspect, the disclosure provides pharmaceutical composition comprising the compound of as described here and a pharmaceutically acceptable carrier.

In another aspect, the disclosure provides a method for treating or inhibiting development of one or more AGE- and/or ALE-associated complications in subject in need thereof comprising administering one or more compounds as described herein to the subject.

In another aspect, the disclosure provides a method for treating or inhibiting development of one or more AGE- and/or ALE-associated complications in a subject in need thereof comprising administering one or more pharmaceutical compositions as described herein to the subject.

In one embodiment, the one or more AGE- and/or ALE-associated complications are selected from the group consisting of accelerated protein aging, retinopathy, nephropathy, proteinuria, impaired glomerular clearance, neuropathy, hyperlipidemia, hypertriglyceridemia, hypercholesterolemia, atherosclerosis, cardiovascular disease, neurodegenerative amyloid diseases, diabetes-associated hyperlipidemia, oxidative modification of proteins, arthritis, connective tissue diseases, amyloidosis, obesity-related complications, proliferation of smooth muscle cells in the aorta, coronary artery occlusion, hypertension; and dialysis-related disorders selected from the group consisting of dialysis-related cardiac morbidity and mortality, dialysis-related amyloidosis, dialysis-related increases in permeability of the peritoneal membrane in a dialysis patient, renal failure progression in a dialysis patient, and ultrafiltration failure and peritoneal membrane destruction in a dialysis patient.

In another aspect, the disclosure provides a method for treating or inhibiting development of one or more disorders selected from the group consisting of diabetic nephropathy, proteinuria, impaired glomerular clearance, retinopathy, neuropathy, atherosclerosis, diabetes-associated hyperlipidemia, oxidative modification of proteins, arthritis, connective tissue diseases, amyloidosis, obesity-related complications proliferation or smooth muscle cells in the aorta, coronary artery occlusion, and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient, wherein the method comprises administering an effective amount of a compound as described herein to a subject in need of such treatment.

In another aspect, the disclosure provides a method for treating or inhibiting development of one or more disorders selected from the group consisting of diabetic nephropathy, proteinuria, impaired glomerular clearance, retinopathy, neuropathy, atherosclerosis, diabetes-associated hyperlipidemia, oxidative modification of proteins, arthritis, connective tissue diseases, amyloidosis, obesity-related complications proliferation or smooth muscle cells in the aorta, coronary artery occlusion, and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient, wherein the method comprises administering an effective amount of a pharmaceutical composition as described herein to a subject in need of such treatment.

In a further aspect, the present disclosure provides pharmaceutical compositions comprising one or more compounds of the disclosure, as disclosed above and a pharmaceutically acceptable carrier. Preferred embodiments of the pharmaceutical compositions are described below.

In a further aspect, the present disclosure provides methods for treating or inhibiting development of one or more AGE- and/or ALE-associated complications in subject in need thereof comprising administering one or more compounds or pharmaceutical compositions of the disclosure to a subject in need thereof. As used herein, the phrase "AGE and/or ALE associated complications" includes, but is not limited to accelerated protein aging, retinopathy, nephropathy, proteinuria, impaired glomerular clearance, neuropathy, hyperlipidemia, hypertriglyceridemia, hypercholesterolemia, atherosclerosis, cardiovascular disease, and neurodegenerative amyloid diseases, such as Alzheimer's disease, diabetes-associated hyperlipidemia, oxidative modification of proteins, arthritis, connective tissue diseases, amyloidosis, obesity-related complications proliferation or smooth muscle cells in the aorta, coronary artery occlusion, oxidative stress-related conditions, and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient.

In a further aspect, the disclosure provides methods for treating or inhibiting development of one or more of diabetic nephropathy, proteinuria, impaired glomerular clearance, retinopathy, neuropathy, atherosclerosis, diabetes-associated hyperlipidemia, oxidative modification of proteins, arthritis, connective tissue diseases, amyloidosis, obesity-related complications proliferation or smooth muscle cells in the aorta, coronary artery occlusion, oxidative stress-related disorders and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient, wherein the methods comprise administering an effective amount of one or more compounds of the present disclosure, or a pharmaceutically acceptable salt thereof, to a subject in need of such treatment.

In a preferred embodiment, the methods are used to treat patients suffering from hyperlipidemia and/or hyperglycemia or their complications, or to inhibit development of complications arising from hyperlipidemia and/or hyperglycemia, such as those described above.

While the methods of this aspect of the present disclosure are not limited by a specific mechanism, it is believed that the compounds of the disclosure are useful in treating or inhibiting development of these complications based on their ability to inhibit AGE and/or ALE formation, and thus to inhibit the development or progression of complications associated with accumulation of AGEs and/or ALEs.

Definitions

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the term "inhibiting development of" means to prevent or to minimize development of the disorder or complication in individuals at risk of developing the disorder or complication.

The term "absent" as used herein means the group is replaced by a single bond. If replacing the group with a bond results in two connected moieties both defined as bonds, then -bond-bond- groups are understood to reduce to a single bond.

The term "alkenyl" as used herein, means a straight or branched chain hydrocarbon containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkanoyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means phenyl or a bicyclic aryl or a tricyclic aryl. The bicyclic aryl is naphthyl, or a phenyl fused to a cycloalkyl, or a phenyl fused to a cycloalkenyl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, azulenyl, dihydroanthracenyl, fluorenyl, and tetrahydrophenanthrenyl.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aroyl" as used herein, means an aryl group, as defined herein, appended to the parent molecular moiety through a carbonyl group, as defined herein. Representative examples of arylcarbonyl include, but are not limited to, benzoyl and naphthoyl.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The term "cycloalkanoyl" as used herein, means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The term "heteroaryloyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-S-ylcarbonyl, pyrimidin-2-ylcarbonyl, thien-2-ylcarbonyl, and thien-3-ylcarbonyl.

The term "heterocycle" as used herein, means a monocyclic, and 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The heterocycle is connected to the parent molecular moiety through any carbon atom or any nitrogen atom contained within the monocyclic heterocycle. Representative examples of heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "heterocycloyl" as used herein, means a heterocycle, as defined herein, appended to the parent molecular moiety through a carbonyl group, as defined herein.

"Oxidative stress" is defined as specific increases in reactive oxygen species and derived free radicals. Oxidative stress related conditions include, but are not limited to atherosclerosis, ischemia-reperfusion injury, inflammatory diseases such as arthritis, cancer, exposure to ionizing radiation and/or chemotherapeutic agents, pulmonary adult respiratory distress syndrome (ARDS), myocardial infarction and strokes, pancreatitis, or intestinal ulceration, and aging. (See, for example, U.S. Pat. Nos. 5,700,654 and 5,462,946).

The term "oxide" as used herein, means an —O moiety; for example, attachment of an oxide group to a nitrogen forms an N-oxide compound, as is familiar to those skilled in the art. In such compounds, the oxygen has a formal negative charge and the nitrogen has a formal positive charge, therefore, the entire compound has a zero net charge.

The term "oxo" as used herein, means an =O moiety.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts. Those skilled in the art will recognize that the salt may be present in various stoichiometry relative to the compound, such as 1:1 1:2, 1:3, 2:1, 3:1, etc. stoichiometry.

In certain embodiments, the compound of the disclosure as described herein is in form of a hydrochloride salt. For example, the compound may be in form of a mono hydrochloride salt, in form of a bis-hydrochloride salt, or in form of a tris-hydrochloride salt.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}F$. Similarly, compounds may be enriched in the heavy isotopes of hydrogen: deuterium and tritium; and similarly can be enriched in a radioactive isotope of nitrogen such as $^{15}N$, or carbon, such as $^{13}C$. Such isotopic variant compounds may undergo different metabolic pathways and can be useful, for example, in studying the ubiquitination pathway and its role in disease. Of course, in certain embodiments, the compound has substantially the same isotopic character as naturally-occurring materials. In certain embodiments, the compounds are isotopically enriched, e.g., in a form enriched in $^{15}N$.

Pharmaceutical Compositions and Administration

The instant compounds can be administered individually or in combination, usually in the form of a pharmaceutical composition. Such compositions are prepared in a manner well known in the pharmaceutical art and comprise at least one active compound.

The compounds of the disclosure can be administered as the sole active pharmaceutical agent, or they can be used in combination with one or more other compounds useful for carrying out the methods of the disclosure, including but not limited to pyridoxamine, aminoguanidine, compounds disclosed in WO 2004/019889 (including but not limited to BST 4996, BST 4997, and BST-146; agents that promote glycemic control, such as insulin, metformin, and thiazolidinediones; and anti-hypertensives such as angiotensin converting enzyme inhibitors (ACEI), angiotensin II receptor blockers (ARB), endothelin receptor antagonists and rennin inhibitors. When administered as a combination, the therapeutic agents can be formulated as separate compositions that are given at the same time or different times, or the therapeutic agents can be given as a single composition.

The compounds may be made up in a solid form (including granules, powders or suppositories) or in a liquid form (e.g., solutions, suspensions, or emulsions). The compounds of the disclosure may be applied in a variety of solutions and may be subjected to conventional pharmaceutical operations such as sterilization and/or may contain conventional adjuvants, such as preservatives, stabilizers, wetting agents, emulsifiers, buffers etc.

The compounds of the disclosure may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the disclosure and a pharmaceutically acceptable carrier. One or more compounds of the disclosure may be present in association with one or more non-toxic pharmaceutically acceptable carriers and/or diluents and/or adjuvants, and if desired other active ingredients. The pharmaceutical compositions containing compounds of the disclosure may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the disclosure may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds and pharmaceutical compositions of the present disclosure may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds and pharmaceutical compositions of the present disclosure may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.01 mg to about 50 mg per kilogram of body weight per day, more preferably between 0.1 mg to about 50 mg per kilogram of body weight per day, and even more preferably between about 0.1 mg to about 20 mg per kilogram of body weight per day are useful in the treatment of the above-indicated conditions. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions containing the compounds described herein are administered to an individual in need thereof. In a preferred embodiment, the subject is a mammal; in a more preferred embodiment, the subject is a human. In therapeutic applications, compositions are administered in an amount sufficient to carry out the methods of the disclosure. Amounts effective for these uses depend on factors including, but not limited to, the nature of the compound (specific activity, etc.), the route of administration, the stage and severity of the disorder, the weight and general state of health of the subject, and the judgment of the prescribing physician. The active compounds are effective over a wide dosage range. However, it will be understood that the amount of the compound actually administered will be determined by a physician, in the light of the above relevant circumstances. Therefore, the above dosage ranges are not intended to limit the scope of the disclosure in any way.

For administration to non-human mammals, the composition may also be added to the animal feed or drinking water. It may be convenient to formulate these animal feed and drinking water compositions so that the animal ingests an appropriate quantity of the composition during a meal or throughout the course of the day. It may also be convenient to present the composition as a premix for addition to the feed or drinking water.

Preparation of Compounds of the Disclosure

The compounds and processes of the present disclosure will be better understood in connection with the following synthetic schemes which illustrate the methods by which the compounds of the disclosure may be prepared. Starting materials can be obtained from commercial sources or prepared by well-established literature methods known to those of ordinary skill in the art.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

It will also be recognized that another major consideration in the planning of any synthetic route in this field is the judicious choice of the protecting group used for protection of the reactive functional groups present in the compounds described in this disclosure. An authoritative account describing the many alternatives to the trained practitioner is Greene and Wuts (Protective Groups In Organic Synthesis, Wiley and Sons, 1999). Suitable protecting groups include, but are not limited to, tert-butoxycarbonyl (BOC), trimethylsilylethanesulfonamide (SES), benzyloxycarbonyl (CBZ) and benzyl (Bn) protecting groups.

Examples

The methods of the disclosure are illustrated further by the following examples, which is not to be construed as limiting the disclosure in scope or spirit to the specific procedures and compounds described in them.

General Procedures: Nuclear magnetic resonance spectra for proton (1H NMR) were recorded and analyzed using Varian 200 (200 MHz) NMR system. The chemical shift (δ) values are expressed in ppm (parts per million) relative to tetramethylsilane as an internal standard: s, singlet; p, pentet; m, multiplet; br, broad singlet. HPLC separation was used to determine the purities of the target compounds. HPLC analysis was performed on a Agilent technologies 1260 infinity system using Agilent® Eclipse XDB-Phenyl column. Absorbance (254 nm) peak area of the major peak versus other peaks was used to determine purity. LCMS analysis was performed on a Finnigan Mat® LCQ LC/MS system using Agilent® EC-C18 column. The following conditions were applied for the LC-MS analyses: Solvent A: 0.1% TFA in $H_2O$, solvent B: 0.1% TFA in ACN; flow rate: 0.50 ml/min; Gradient: Solvent A (95%, 0-0.5 min), Solvent A (95%-50%, 0.5-5 min), Solvent B (50%, 5-10 min), Solvent B (50-95%, 10-12 min), Solvent B (95%, 12-13 min). All solvents were purchased from Sigma-Aldrich Co. or Fisher Scientific Inc. or Alfa Aesar and were used as received. Pyridoxal hydrochloride, methyl azetidine-3-carboxylate hydrochloride, 1-methyl piperazine were purchased from Combiblocks Inc. Morpholine, pyrrolidine, glyoxal and ammonium hydroxide solution were purchased from Sigma-Aldrich. $^{15}N$-Ammonium hydroxide (3.3 M) was purchased from Cambridge Isotope Laboratories.

Four compounds 4, 5, 8 and 9 in milligram quantities were made based on the chemistry shown in Scheme 1 below. From these four, two compounds (5 and 8) were synthesized up to 25 g scale and $^{15}N$-labelled compounds 13 and 14 were also synthesized. The synthetic schemes as well as the experimental procedures for the synthesis of the final compounds from the previously synthesized intermediates were presented below.

Scheme 1.

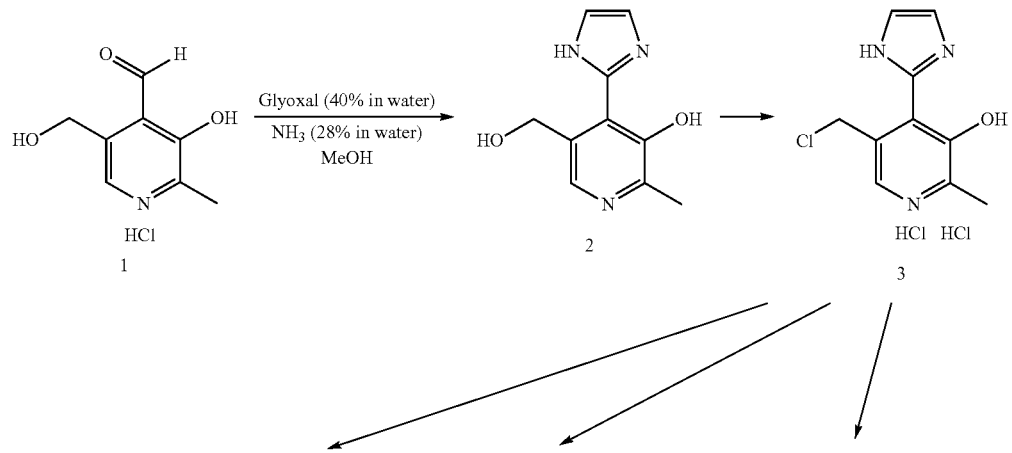

23

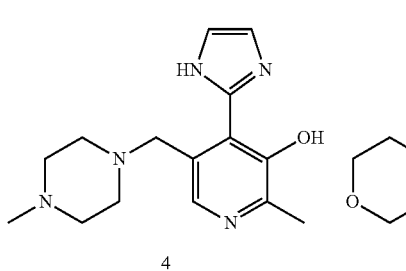

4

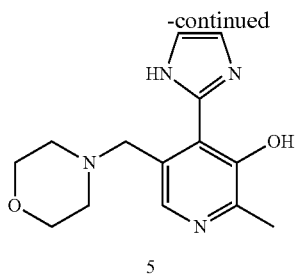

5

24

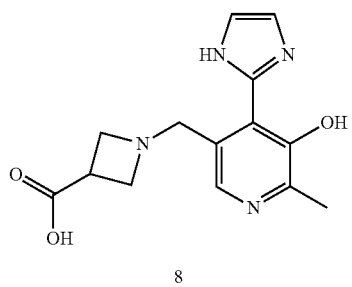

8

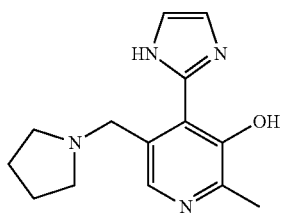

9

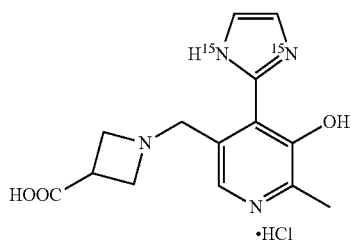

13

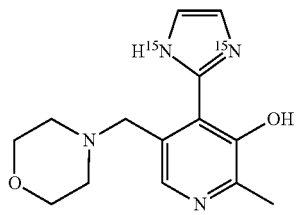

14

Pyridoxal hydrochloride 1 was treated with glyoxal (40%) and ammonium hydroxide (28%) at room temperature to obtain imidazole derivative 2. It was treated with thionyl chloride in toluene under reflux conditions to obtain imidazole derivative 3. Imidazole derivative 3 was treated with N-methyl piperazine, morpholine and pyrrolidine at room temperature to obtain final compounds 4, 5 and 9 respectively. To obtain final compound 8, imidazole derivative 3 was first treated with methyl azetidine-3-carboxylate hydrochloride in the presence of triethylamine at room temperature followed by hydrolysis of obtained methyl ester derivative 7 to give methyl azetidine-3-carboxylate 8.

Two compounds (5 and 8) were synthesized up to 25 g scale using above synthetic route. To synthesize $^{15}$N-labelled compounds 5 and 8 (Scheme 2), pyridoxal hydrochloride 1 was treated with glyoxal (40%) and $^{15}$N-ammonium hydroxide (3.3 M) at room temperature to obtain imidazole derivative 10. It was treated with thionyl chloride in toluene under reflux conditions to obtain imidazole derivative 11. It was then treated with morpholine at room temperature to obtain final compound 14. To obtain final compound 13, imidazole derivative 11 was first treated with methyl azetidine-3-carboxylate hydrochloride in the presence of triethylamine at room temperature followed by hydrolysis of obtained methyl ester derivative 12 to give $^{15}$N-labelled azetidine-3-carboxylic acid derivative 13.

Scheme 2.

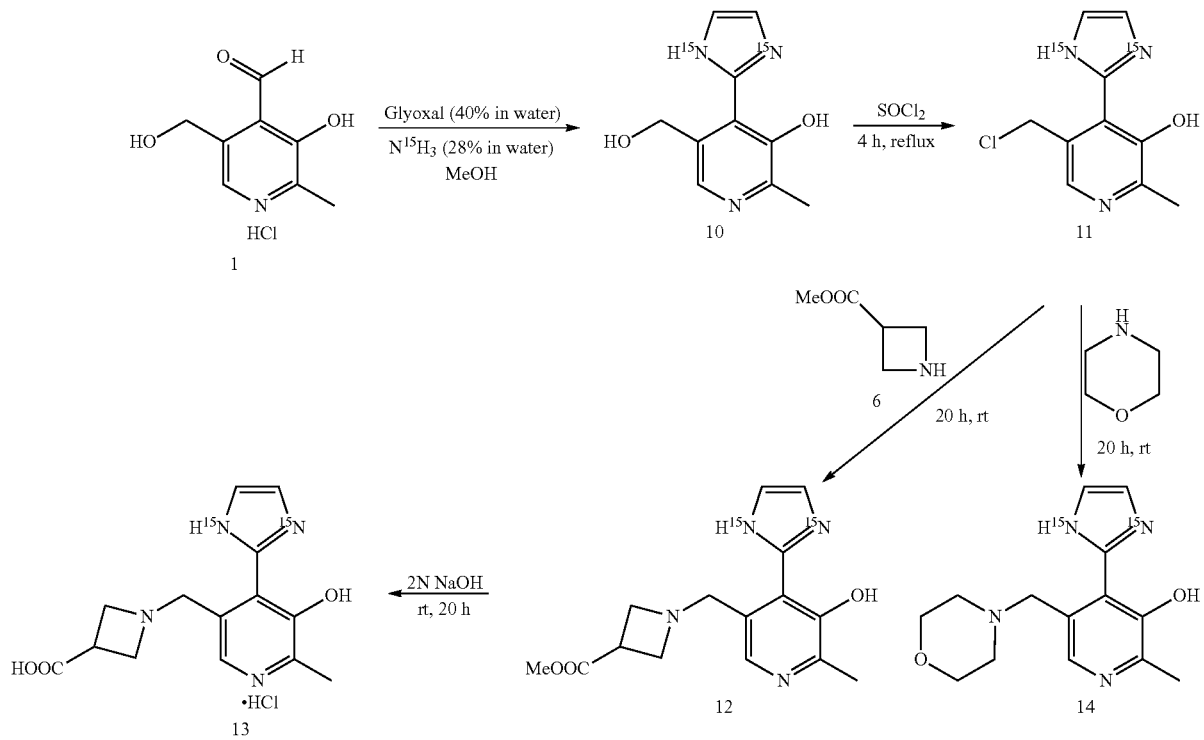

All the four compounds 4, 5, 8, 9 were purified by column chromatography and obtained as their free base except compound 8, which was obtained as a HCl salt. Scale-up of compounds 5 and 8 were also done successfully. Compound 8 was purified by crystallization during its scale-up process. $^{15}$N-Labelled compounds 14 as a free base and 13 as a HCl salt were also synthesized successfully and purified by column chromatography.

Example 1. Synthesis of Imidazole Derivative 2 (PTG-4997, CV-10206)

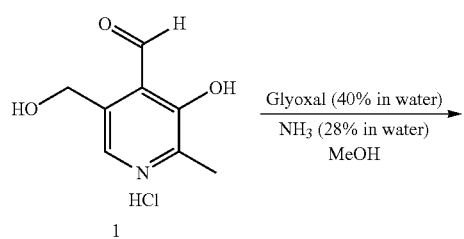

To pyridoxal hydrochloride 1 (1 eq.) in methanol (12 vol), which was cooled to 5° C. C using NaCl/Ice bath was added glyoxal solution (40%, 4 vol). Then solution of ammonia (28%, 4 vol) was added dropwise keeping the temperature between 5-10° C. The beginning slightly yellow homogeneous mixture became a red color. After complete addition, the mixture was stirred for additional 4 h at 5° C. and the reaction mixture was stirred for overnight at room temperature. After completion of the reaction, mixture was filtered to remove some solid particles present and the methanol was evaporated at 35° C. The aqueous layer was extracted six times with ethyl acetate. The combined organic layers were washed with water, brine and dried over sodium sulphate. Evaporation of solvent gave crude compound, which was stirred 40 mins with 1:1 ethyl acetate and diethyl ether mixture. The resulting solid was filtered and washed with diethyl ether and dried to obtain imidazole derivative 2 as light brown solid. Yield: 33%; 1H NMR (200 MHz, CD3OD): δ=2.51 (s, 3H, CH3), 4.70 (s, 2H, CH2), 7.32-7.35 (m, 2H, Ar), 7.84 (s, 1H, Ar). LCMS (ESI): m/z calculated for C10H11N3O2+H+[M+H+]: 206.1; Found: 206.1. HPLC purity: 92.4% (at 254 nm).

Example 2. Synthesis of Imidazole Derivative 3 (PTG-520, CV-10223)

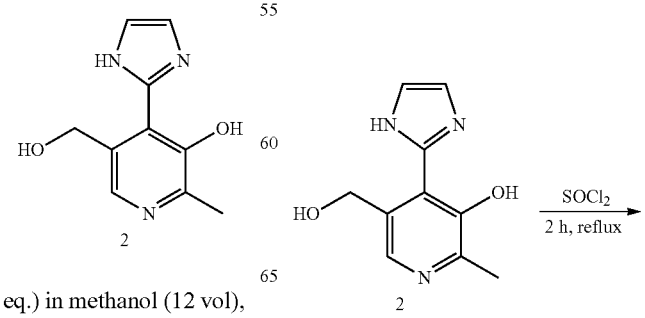

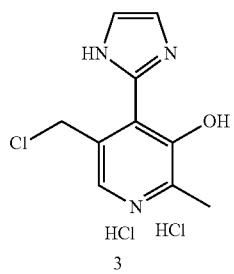

To imidazole derivative 2 (1 eq.) in toluene (20 vol) was added thionyl chloride (5 vol) and the mixture was refluxed for 2 h. Reaction mixture was cooled to 0° C. and filtered, washed with cold toluene to give imidazole derivative 3 as brown solid, which was used without further purification. Yield: 83%; 1H NMR (200 MHz, CD3OD): δ=2.79 (s, 3H, CH3), 4.81 (s, 2H, CH2), 7.92 (s, 2H, Ar), 8.58 (s, 1H, Ar).

Example 3. Synthesis of Imidazole Derivatives 4, 5 and 9

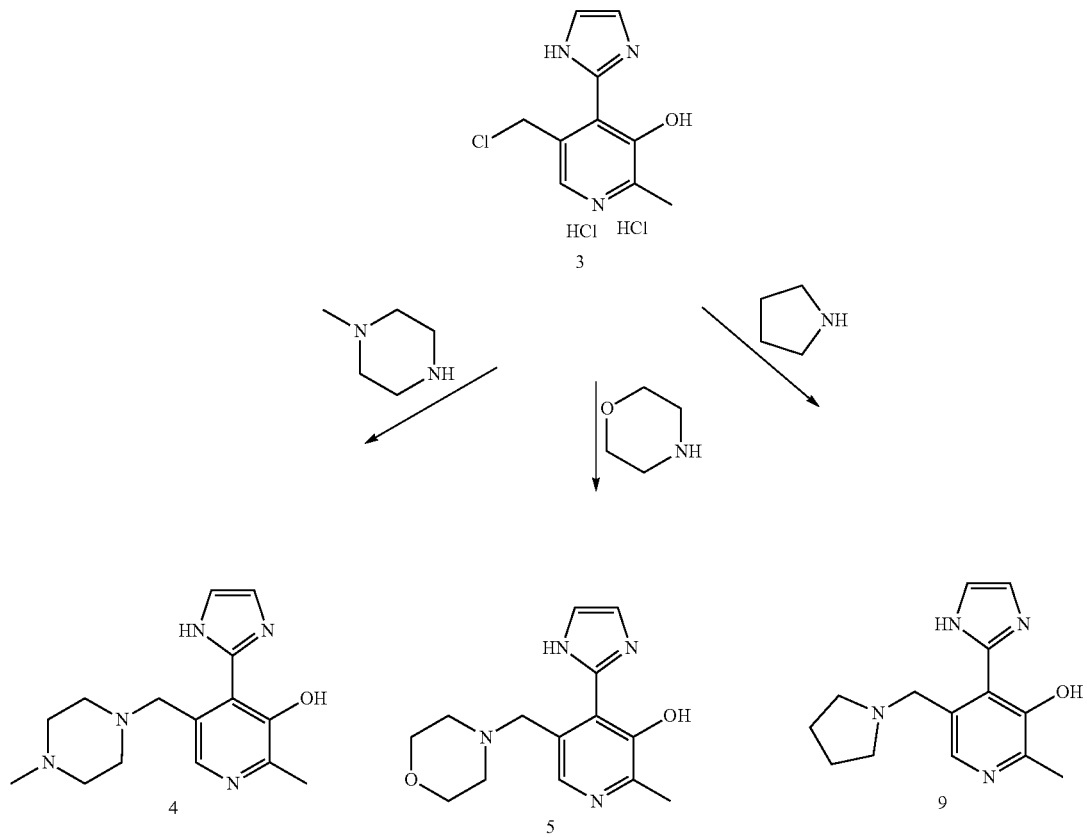

General procedure to synthesize compounds 4, 5, and 9: To imidazole derivative 3 (1 eq.) in methylene chloride (42 vol.) was added N-methyl piperazine or morpholine or pyrrolidine (10 eq.) and mixture was stirred at room temperature for 20 h. The reaction mixture was concentrated and dissolved in methylene chloride. Methylene chloride solution was washed with water, and brine solution and dried over sodium sulfate. Solvent was concentrated, and residue was purified using Combiflash Rf (0-5% of methanol in methylene chloride) and the fractions containing the pure product (TLC) were pooled and evaporated to provide pure products 4, 5, and 9.

N-Methyl piperazine derivative 4 (CV-10191, PTG-605). Light brown solid; yield: 28.4%; 1H NMR (200 MHz, CDCl$_3$): δ=2.31 (s, 3H, CH$_3$), 2.40-2.80 (br s, 11H, (CH$_2$)$_4$, CH$_3$), 3.63 (s, 2H, CH2), 7.14 (s, 1H, Ar), 7.24-7.25 (m, 1H, Ar), 7.87 (s, 1H, Ar). LCMS (ESI): m/z calculated for C$_{15}$H$_{21}$N$_5$O+H$^+$[M+H$^+$]: 288.2; Found: 288.2. HPLC purity: 99.5% (at 254 nm).

N-Morpholine derivative 5 (CV-10192, PTG-630). Light brown solid; yield: 45%; 1H NMR (200 MHz, CDCl3): δ=2.56 (s, 3H, CH3), 2.64 (br s, 4H, (CH2)2), 3.66 (s, 2H, CH2), 3.77 (br s, 4H, (CH2)2), 7.16 (s, 1H, Ar), 7.25-7.26 (m, 1H, Ar), 7.89 (s, 1H, Ar). LCMS (ESI): m/z calculated for C14H18N4O2+H+[M+H+]: 275.1; Found: 275.2. HPLC purity: 96.3% (at 254 nm).

N-Pyrrolidine derivative 9 (CV-10215, PTG-650). Light brown solid; yield: 47%; 1H NMR (200 MHz, CDCl3): δ=1.85-1.91 (m, 4H, (CH2)2), 2.56 (s, 3H, CH3), 2.67 (br s, 4H, (CH2)2), 3.73 (s, 2H, CH2), 7.12-7.13 (m, 1H, Ar), 7.23-7.26 (m, 1H, Ar), 7.90 (s, 1H, Ar). LCMS (ESI): m/z calculated for C14H18N4O+H+[M+H+]: 259.3; Found: 259.2. HPLC purity: 95.0% (at 254 nm).

Example 4. Synthesis of Azetidine 3-Carboxylic Acid Derivative 8

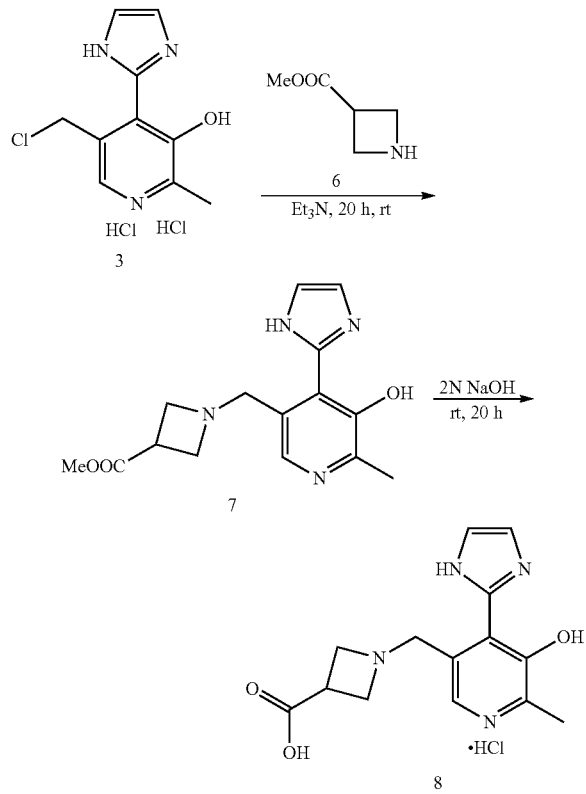

To imidazole derivative 3 (1 eq.) in methylene chloride (40 vol) were added 3-methyl azetidine carboxylate (1.5 eq), triethyl amine (8 eq.) and mixture was stirred at room temperature for 20 h. The reaction mixture was concentrated and dissolved in methylene chloride. Organic layer was washed with water, and brine solution and dried over sodium sulfate. Solvent was concentrated, and residue was purified using Combiflash Rf (0-5% of methanol in methylene chloride) and the fractions containing the pure product (TLC) were pooled and evaporated to provide pure product 7.

3-Methyl azetidine carboxylate derivative 7 (PTG-641, CV-10224). Brown gel; yield: 41%; 1H NMR (200 MHz, CDCl3): δ=2.45 (s, 3H, CH3), 3.28-3.64 (m, 5H, (CH2)2, CH), 3.72 (s, 3H, CH3), 4.94 (br s, 1H, NH), 7.30-7.31 (m, 2H, Ar), 7.87 (s, 1H, Ar). LCMS (ESI): m/z calculated for C15H18N4O3+H+[M+H+]: 303.3; Found: 303.1.

To 3-methyl azetidine carboxylate derivative 7 (1 eq.) in THF-water (1:1) (24 vol combined) was added 2 N NaOH (2 eq.) solution and mixture was stirred at room temperature for 20 h. The reaction mixture was concentrated and dissolved in water and acidified up to pH 4-5. Mixture was concentrated, and residue was purified using Combiflash Rf (Chloroform: methanol: water—16:6:1) and the fractions containing the pure product (TLC) were pooled and evaporated to provide pure product 8. During the scale-up of this product, the crude residue was purified by treatment with 1:1 water-methanol and formed solid was filtered and washed with methanol and dried.

Azetidine 3-carboxylic acid derivative 8 (CV-10193, PTG-640). Light yellow solid; yield: 66%; 1H NMR (200 MHz, D2O): δ=2.59 (s, 3H, CH3), 3.62 (p, 1H, CH), 4.14-4.38 (m, 4H, (CH2)2,), 4.50 (s, 2H, CH2), 7.51 (m, 2H, Ar), 7.89 (s, 1H, Ar). LCMS (ESI): m/z calculated for C14H16N4O3+H+[M+H+]: 289.1; Found: 289.1.

Example 5. Synthesis of $^{15}$N-Labelled Compounds 13 and 14

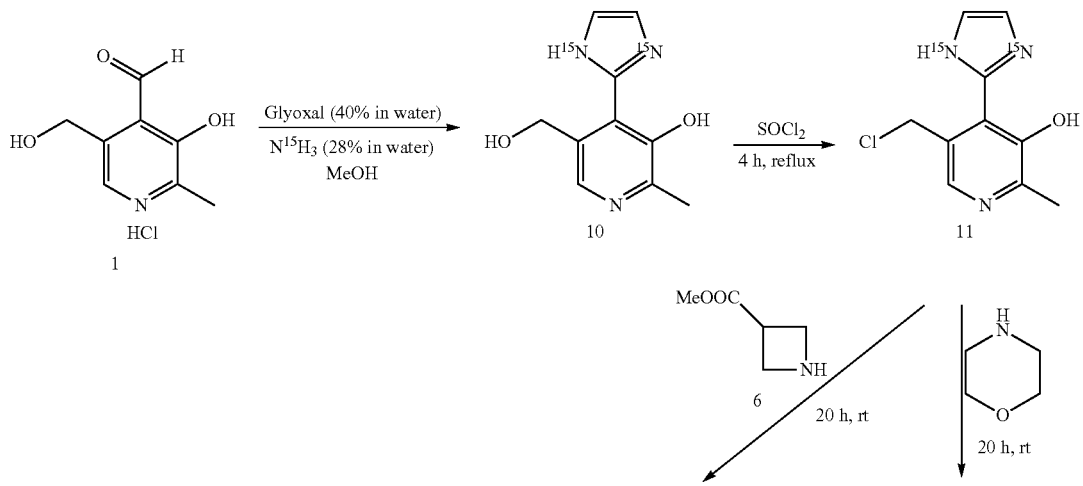

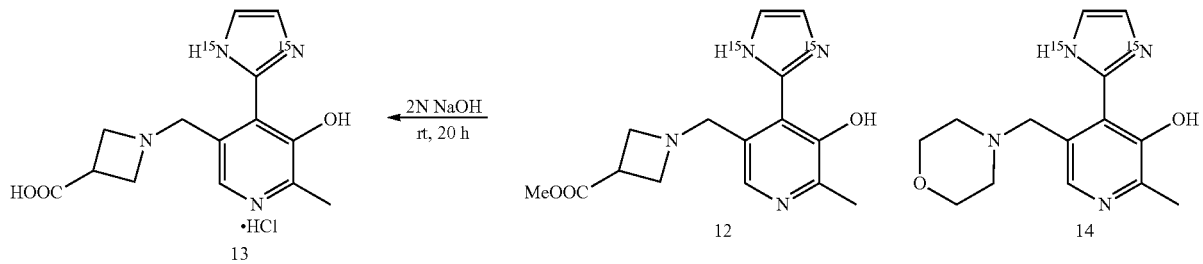

Imidazole derivative 10: To pyridoxal hydrochloride 1 (1 eq.) in methanol (12 vol), which was cooled to 5° C. using NaCl/Ice bath was added glyoxal solution (40%, 4 vol). Then solution of $^{15}$N-ammonium hydroxide (3.3 M, 10 vol) was added dropwise keeping the temperature between 5-10° C. The beginning slightly yellow homogeneous mixture became a red color. After complete addition, the mixture was stirred for additional 4 h at 5° C. and the reaction mixture was stirred for overnight at room temperature. After completion of the reaction, the methanol was evaporated at 35° C. The aqueous layer was extracted six times with ethyl acetate. The combined organic layers were washed with water, brine and dried over sodium sulphate. Evaporation of solvent gave crude compound, which was stirred 40 mins with 1:1 ethyl acetate and diethyl ether mixture. The resulting solid was filtered and washed with diethyl ether and dried to obtain imidazole derivative 10 as light brown solid. Yield: 26.5%; 1H NMR (200 MHz, CD3OD): δ=2.49 (s, 3H, CH3), 4.71 (s, 2H, CH2), 7.30-7.35 (m, 2H, Ar), 7.85 (s, 1H, Ar). LCMS (ESI): m/z calculated for $C_{10}H_{11}NN^{15}{}_2O_2+H^+[M+H^+]$: 208.1; Found: 208.1.

Imidazole derivative 11. To imidazole derivative 10 (1 eq.) in toluene (20 vol) was added thionyl chloride (5 vol) and the mixture was refluxed for 2 h. Reaction mixture was cooled to 0° C. and filtered, washed with cold toluene to give imidazole derivative 11 as brown solid, which was used without further purification. Yield: 38%; 1H NMR (200 MHz, CD3OD): δ=2.63 (s, 3H, CH3), 4.54 (s, 2H, CH2), 7.60 (s, 2H, Ar), 8.02 (s, 1H, Ar). LCMS (ESI): m/z calculated for $C_{10}H_{10}NN^{15}{}_2O+H^+[M+H^+]$: 226.1; Found: 226.1.

Synthesis of $^{15}$N-labelled compound 14: To imidazole derivative 11 (1 eq.) in methylene chloride (50 vol) was added morpholine (10 eq.) and mixture was stirred at room temperature for 20 h. The reaction mixture was concentrated and dissolved in methylene chloride. Organic layer was washed with water, and brine solution and dried over sodium sulfate. Solvent was concentrated, and residue was purified using Combiflash Rf (0-5% of methanol in methylene chloride) and the fractions containing the pure product (TLC) were pooled and evaporated to provide pure product 14.

$^{15}$N-Morpholine derivative 14 (CV-10212, $^{15}$N-labeled PTG-630). Light yellow gel; yield: 62.7%; 1H NMR (200 MHz, CDCl3): δ=2.56 (s, 3H, CH3), 2.65 (br s, 4H, (CH2)2), 3.66 (s, 2H, CH2), 3.77 (br s, 4H, (CH2)2), 7.14-7.19 (m, 1H, Ar), 7.23-7.30 (m, 1H, Ar), 7.89 (s, 1H, Ar). LCMS (ESI): m/z calculated for $C_{14}H_{18}N_2{}^{15}N_2O_2+H^+[M+H^+]$: 277.3; Found: 277.2. HPLC purity: 94.0% (at 254 nm).

Example 6. Synthesis of $^{15}$N-Labelled Azetidine 3-Carboxylic Acid Derivative 13

To imidazole derivative 11 (1 eq.) in methylene chloride were added 3-methyl azetidine carboxylate (1.5 eq.), triethyl amine (8 eq.) and mixture was stirred at room temperature for 20 h. The reaction mixture was concentrated and dissolved in methylene chloride. Organic layer was washed with water, and brine solution and dried over sodium sulfate. Solvent was concentrated, and residue was purified using Combiflash Rf (0-5% of methanol in methylene chloride) and the fractions containing the pure product (TLC) were pooled and evaporated to provide pure product 12.

3-Methyl azetidine carboxylate derivative 12. Brown gel; yield: 45%; 1H NMR (200 MHz, CDCl3): δ=2.55 (s, 3H, CH3), 3.25-3.40 (m, 1H, CH), 3.53-3.57 (m, 4H, (CH2)2), 3.69-3.74 (m, 5H, CH3, CH2), 7.22-7.26 (m, 2H, Ar), 7.91 (s, 1H, Ar). LCMS (ESI): m/z calculated for $C15H18N4O3+H^+[M+H^+]$: 305.1; Found: 305.1.

To 3-methyl azetidine carboxylate derivative 12 (1 eq.) in THF-water (1:1) was added 2 N NaOH (2 eq.) solution and mixture was stirred at room temperature for 20 h. The reaction mixture was concentrated and dissolved in water and acidified up to pH 4-5. Mixture was concentrated, and residue was purified using Combiflash Rf (Chloroform:methanol: water—16:6:1) and the fractions containing the pure product (TLC) were pooled and evaporated to provide pure product 13.

$^{15}$N-Labeled azetidine 3-carboxylic acid derivative 13 (CV-10213, $^{15}$N-labeled PTG-640): Light yellow solid; yield: 66%; 1H NMR (200 MHz, D2O): δ=2.58 (s, 3H, CH3), 3.25-3.42 (m, 1H, CH), 4.18-4.40 (m, 4H, (CH2)2,), 4.59 (s, 2H, CH2), 7.41-7.45 (m, 2H, Ar), 7.79 (s, 1H, Ar). LCMS (ESI): m/z calculated for $C_{14}H_{16}{}^{15}N_2N_2O_3+H^+[M+H^+]$: 291.1; Found: 291.1. HPLC purity: 91.4% (at 254 nm).

Example 7. Synthesis of Imidazole Derivatives 15 and 16

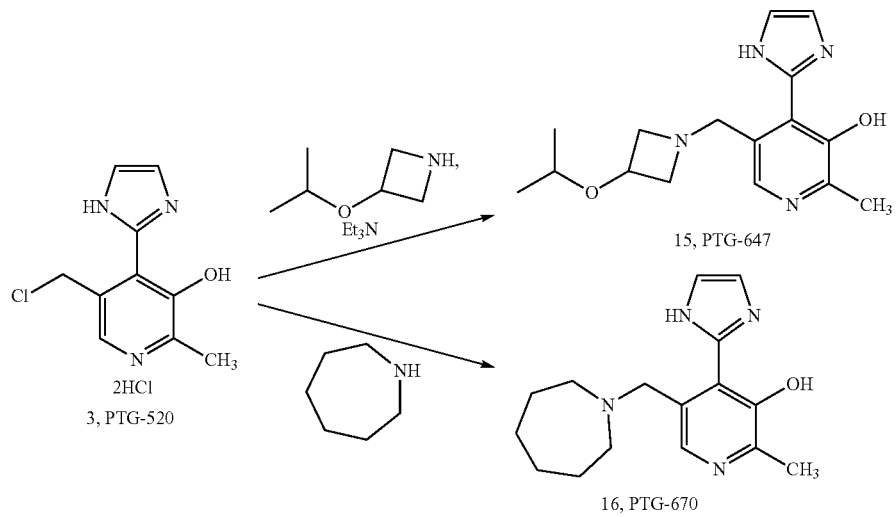

Azetidine isopropyl ether hydrochloride (1.5 eq.) and triethylamine (5 eq.) were added to chloro imidazole 3 in methylene chloride (42 vol) and mixture was stirred at room temperature for 20 h. The reaction mixture was concentrated and dissolved in methylene chloride. Organic layer was washed with water, and aq. brine solution and dried over sodium sulfate. Solvent was concentrated, and residue was purified using Combiflash $R_f$ (0-5% of methanol in methylene chloride) and the fractions containing the pure product (TLC) were pooled and evaporated to provide pure product.

N-Isopropoxy-azetidine derivative 15 (SPNC-096, PTG-647, 2060-SRT-68). Brown solid; yield: 31.3%; $^1$H NMR (300 MHz, CDCl$_3$): δ=1.12 (d, 6H, J=5.7 Hz (CH$_3$)$_2$), 2.54 (s, 3H, CH$_3$), 3.13-3.18 (m, 2H, (CH$_2$)), 3.54-3.72 (m, 5H, CH, (CH$_2$)$_2$), 4.20-4.24 (m, 1H, CH), 7.15-7.21 (m, 2H, Ar), 7.90 (s, 1H, Ar). $^{13}$C NMR (75 MHz, CDCl$_3$): δ=19.5, 22.5, 60.0, 61.5, 66.2, 71.5, 110.0, 117.5, 118.5, 123.3, 127.2, 140.6, 145.5, 149.6, 150.9. LCMS (ESI): m/z calculated for C$_{16}$H$_{22}$N$_4$O$_2$+H$^+$[M+H$^+$]: 303.17; Found: 303.01. HPLC purity: 99.4% (at 254 nm).

N-Hexamethyleneimine derivative 16 (PTG-670 as free base). Brown gel; yield: 53.4%; $^1$H NMR (300 MHz, CDCl$_3$): δ=1.66 (s, 8H, (CH$_2$)$_4$), 2.56 (s, 3H, CH$_3$), 2.76 (br s, 4H, (CH$_2$)$_2$), 3.69 (s, 2H, CH$_2$), 7.13 (s, 1H, Ar), 7.23 (s, 1H, Ar), 7.85 (s, 1H, Ar). $^{13}$C NMR (75 MHz, CDCl$_3$): δ=19.4, 26.8, 27.6, 53.8, 59.5, 117.2, 118.9, 124.4, 127.3, 141.2, 146.0, 149.4, 151.1.

Example 8. Synthesis of Imidazole Derivatives 17 and 18

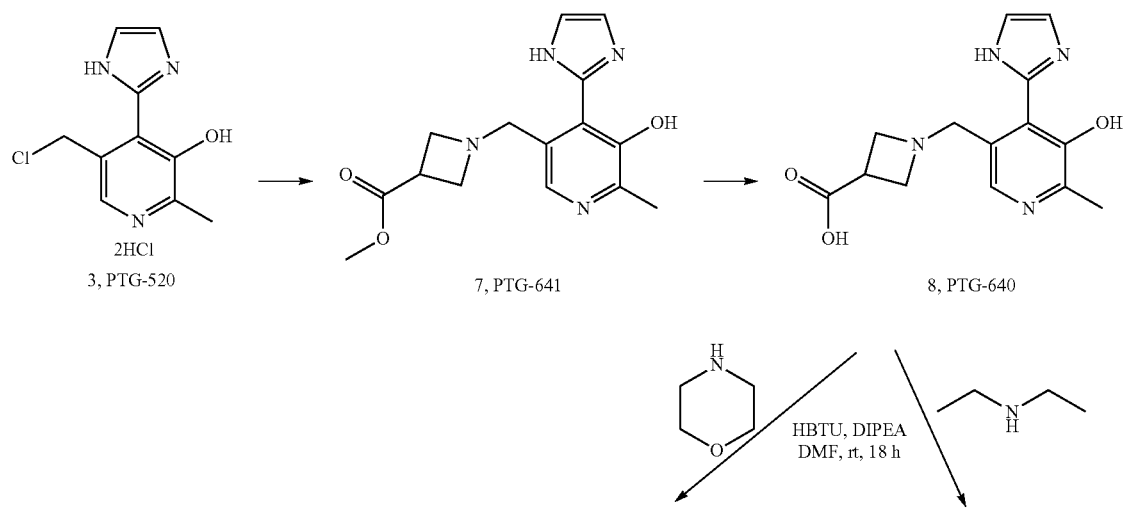

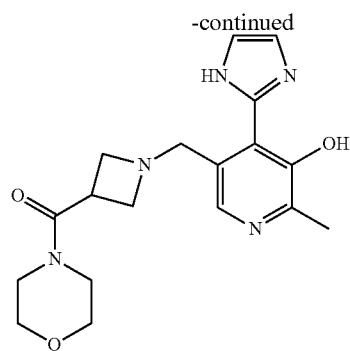

17, PTG-645

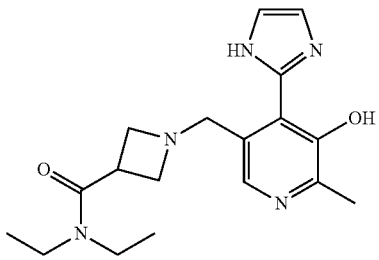

18, PTG-644

To azetidine carboxylic acid derivative 8 (1 eq.) in DMF (20 vol) were added DIPEA (2 eq.), HBTU (1 eq.) followed by morpholine or N,N-diethylamine (1.19 eq) at room temperature and the mixture was stirred at room temperature for 18 h. The reaction mixture was diluted with water (20 vol) and extracted with 10% methanol in DCM (3×25 vol). Organic layer was washed with aq. sodium bicarbonate (12 vol), brine (6 vol) and dried over sodium sulphate. Organic layer was filtered and concentrated to 2.5 vol. Added hexanes (12 vol) and left for 48 h at room temperature. Formed solid was filtered and washed with hexanes (6 vol). The solid was triturated with MTBE (6 vol), 60 ethyl acetate in hexanes (3 vol). The solid was re-dissolved in 10% methanol in DCM and concentrated to get pure compound 17. In the case of compound 18, crude compound was purified using Combiflash $R_f$ (0-10% methanol in DCM) and the fractions containing the pure product (TLC) were pooled and evaporated to provide pure product 18.

N-Azetidine morpholine 3-carboxyamide derivative 17 (SPNC-097, PTG-645, 308-RCH-184-1). Light brown solid; yield: 64.5%; $^1$H NMR (300 MHz, CD$_3$OD): δ=2.47 (s, 3H, CH$_3$), 3.30-3.36 (m, 1H, CH), 3.50-3.69 (m, 12H, (CH$_2$)$_6$), 3.78 (s, 2H, CH$_2$), 7.32 (s, 2H, Ar), 7.89 (s, 1H, Ar). $^{13}$C NMR (75 MHz, DMSO-d$^6$): δ=19.7, 32.4, 42.1, 45.4, 54.9, 58.5, 66.4, 66.5, 118.4, 124.2, 141.3, 145.1, 148.4, 150.4, 170.2. LCMS (ESI): m/z calculated for C$_{18}$H$_{23}$N$_5$O$_3$+H$^+$ [M+H$^+$]: 358.18; Found: 358.08. HPLC purity: 99.4% (at 254 nm).

N-Azetidine N,N-diethyl 3-carboxyamide derivative 18 (SPNC-098, PTG-644, 308-RCH-187-1). Tan solid; yield: 33.5% (Isolated yield); $^1$H NMR (300 MHz, CDCl$_3$): δ=1.13 (t, 6H, J=6.9 Hz, CH$_3$), 2.56 (s, 3H, CH$_3$), 3.15-3.18 (m, 2H, CH$_2$), 3.39-3.41 (m, 2H, CH$_2$), 3.50-3.60 (m, 5H, CH, (CH$_2$)$_2$,), 3.74 (s, 2H, CH$_2$), 7.24-7.27 (m, 2H, Ar), 7.93 (s, 1H, Ar). LCMS (ESI): m/z calculated for C$_{18}$H$_{25}$N$_5$O$_2$+H$^+$ [M+H$^+$]: 344.2; Found: 344.08. HPLC purity: 99.5% (at 254 nm).

Example 9. Synthesis of Salts of Imidazole Derivative 5

To free base derivative 5 (1 eq.) in methylene chloride (10 vol) was added 1M hydrochloride solution in ethyl acetate (1 eq. for compound 19; 2 eq. for compound 20; 3 eq. for compound 21) dropwise at room temperature and mixture was stirred further for 2 h at room temperature. Formed solid was filtered out and washed with ethyl acetate (20 vol), followed by drying under vacuum.

Mono-hydrochloride salt of PTG-630 (19, SPNC-094, 2060-SRT-72). Tan solid; yield: 88%; $^1$H NMR (300 MHz, D$_2$O): δ=2.54 (s, 3H, CH$_3$), 3.16-3.19 (m, 4H, (CH$_2$)$_2$), 3.92-3.96 (s, 4H, (CH$_2$)$_2$), 4.22 (s, 2H, CH$_2$), 7.45 (s, 2H, Ar), 7.67 (s, 1H, Ar). $^{13}$C NMR (75 MHz, D$_2$O): δ=15.4, 49.9, 57.1, 64.6, 122.2, 123.8, 124.9, 125.3, 142.0, 148.1, 161.5. LCMS (ESI): m/z calculated for C$_{14}$H$_{18}$N$_4$O$_2$+H$^+$ [M+H$^+$]: 275.14; Found: 275.01. HPLC purity: 99.7% (at 254 nm). Elemental analysis calculated for C$_{14}$H$_{18}$N$_4$O$_2$·1.05 HCl·0.75 H$_2$O: Carbon: 51.56; hydrogen: 6.35; chloride: 11.41; nitrogen: 17.18; Found: Carbon: 51.81; hydrogen: 6.37; chloride: 11.34; nitrogen: 16.83.

Bis-hydrochloride salt of PTG-630 (20, SPNC-107, 2060-SRT-79). Light green solid; yield: 87%; $^1$H NMR (300 MHz, D$_2$O): δ=2.55 (s, 3H, CH$_3$), 3.14-3.17 (m, 4H, (CH$_2$)$_2$), 3.83-3.86 (s, 4H, (CH$_2$)$_2$), 4.28 (s, 2H, CH$_2$), 7.46 (s, 2H, Ar), 8.01 (s, 1H, Ar). $^{13}$C NMR (75 MHz, D$_2$O): δ=15.7, 50.5, 56.0, 64.1, 123.3, 124.3, 127.9, 130.7, 138.1, 148.1, 156.1. LCMS (ESI): m/z calculated for C$_{14}$H$_{18}$N$_4$O$_2$+H$^+$ [M+H$^+$]: 275.14; Found: 275.01. HPLC purity: 99.6% (at 254 nm). Elemental analysis calculated for C$_{14}$H$_{18}$N$_4$O$_2$·2 HCl·0.1 H$_2$O: Carbon: 48.18; hydrogen: 5.83; chloride: 20.31; nitrogen: 16.05; Found: Carbon: 48.29; hydrogen: 5.94; chloride: 20.15; nitrogen: 15.94.

Tris-hydrochloride salt of PTG-630 (21, SPNC-108, 2060-SRT-80). Brown solid; yield: 50%; $^1$H NMR (300 MHz, D$_2$O): δ=2.59 (s, 3H, CH$_3$), 3.16-3.19 (m, 4H, (CH$_2$)$_2$), 3.83-3.86 (s, 4H, (CH$_2$)$_2$), 4.33 (s, 2H, CH$_2$), 7.52 (s, 2H, Ar), 8.16 (s, 1H, Ar). $^{13}$C NMR (75 MHz, D$_2$O): δ=15.8, 51.0, 55.0, 63.7, 122.9, 125.0, 127.6, 132.4, 135.7, 148.4, 155.1. LCMS (ESI): m/z calculated for C$_{14}$H$_{18}$N$_4$O$_2$+H$^+$[M+H$^+$]: 275.14; Found: 275.03. HPLC purity: 99.4% (at 254 nm). Elemental analysis calculated for C$_{14}$H$_{18}$N$_4$O$_2$·2.7 HCl·1.4H$_2$O·0.35C$_4$H$_8$O: Carbon: 43.13; hydrogen: 6.18; chloride: 22.32; nitrogen: 13.07; Found: Carbon: 43.21; hydrogen: 6.26; chloride: 22.35; nitrogen: 13.06.

Example 10. Synthesis of Salts of Imidazole Derivatives 16 and 7

To free base derivative 16 or 7 (1 eq.) in methylene chloride (10 vol) was added 1M hydrochloride solution in ethyl acetate (1 eq.) dropwise at room temperature and mixture was stirred further for 2 h at room temperature. Formed solid was filtered out and washed with ethyl acetate (20 vol), followed by drying under vacuum.

Mono-hydrochloride salt of PTG-670 (22, SPNC-095, 2060-SRT-69). Tan solid; yield: 77%; $^1$H NMR (300 MHz, D$_2$O): δ=1.55 (br s, 4H, (CH$_2$)$_2$), 1.73 (br s, 4H, (CH$_2$)$_2$), 2.41 (s, 3H, CH$_3$), 3.15 (br s, 4H, (CH$_2$)$_2$), 4.20 (s, 2H, CH$_2$), 4.66 (s, 4H, (CH$_2$)$_2$), 7.27-7.28 (m, 2H, Ar), 7.59 (s, 1H, Ar). $^{13}$C NMR (75 MHz, D$_2$O): δ=15.4, 24.0, 25.8, 52.6, 56.9, 123.3, 123.6, 126.4, 126.7, 141.7, 147.2, 159.8. LCMS (ESI): m/z calculated for $C_{16}H_{22}N_4O+H^+[M+H^+]$: 287.18; Found: 287.03. HPLC purity: 99.7% (at 254 nm). Elemental analysis calculated for $C_{16}H_{22}N_4O·1.2$ HCl·0.3 H$_2$O: Carbon: 57.27; hydrogen: 7.15; chloride: 12.68; nitrogen: 16.7; Found: Carbon: 57.53; hydrogen: 7.22; chloride: 12.67; nitrogen: 16.48.

Mono-hydrochloride salt of PTG-641 (23, SPNC-093, 308-RCH-192-1). Tan solid; yield: 95.4%; $^1$H NMR (300 MHz, CD$_3$OD): δ=2.59 (s, 3H, CH$_3$), 3.65-3.78 (m, 1H, CH), 3.79 (s, 3H, CH$_3$), 4.12-4.24 (m, 4H, (CH$_2$)$_2$), 4.35 (s, 2H, CH$_2$), 7.42 (s, 2H, Ar), 8.01 (s, 1H, Ar). $^{13}$C NMR (75 MHz, D$_2$O): δ=15.5, 32.7, 53.1, 54.1, 55.5, 123.0, 125.2, 126.3, 142.3, 148.2, 161.5, 173.5. LCMS (ESI): m/z calculated for $C_{15}H_{18}N_4O_3+H^+[M+H^+]$: 303.13; Found: 302.95. HPLC purity: 99.7% (at 254 nm). Elemental analysis calculated for $C_{15}H_{18}N_4O_3·1.0$ HCl·0.6H$_2$O: Carbon: 51.53; hydrogen: 5.82; chloride: 10.14; nitrogen: 16.03; Found: Carbon: 51.62; hydrogen: 5.85; chloride: 10.15; nitrogen: 15.96.

Example 11. Synthesis of $^{15}$N-Labelled Compound 24

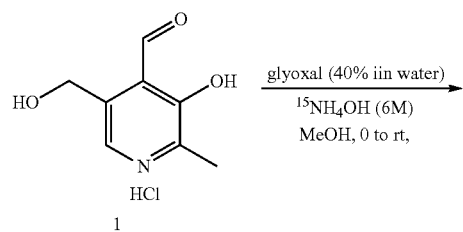

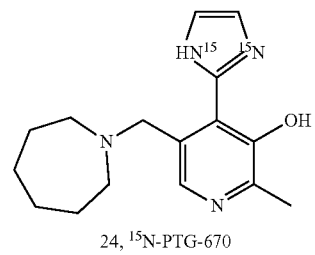

24, $^{15}$N-PTG-670

To $^{15}$N-labelled chloro-pyridyl imidazole derivative 11 (1 eq.) in methylene chloride (50 vol) was added morpholine (10 eq.) or hexamethyleneimine (10 eq.) and mixture was stirred at room temperature for 20 h. The reaction mixture was concentrated and dissolved in methylene chloride. Organic layer was washed with water, and brine solution and dried over sodium sulphate. Solvent was concentrated, and residue was purified using Combiflash R$_f$ (0-5% of methanol in methylene chloride) and the fractions containing the pure product (TLC) were pooled and evaporated to provide pure product 24.

$^{15}$N-Labelled hexamethyleneimine derivative 24 (SPNC-101, $^{15}$N-labeled PTG-670, 2060-SRT-78). Brown gel; yield: 6%; $^1$H NMR (300 MHz, CDCl$_3$): δ=$^1$H NMR (300 MHz, CDCl$_3$): δ=1.63 (br s, 8H, (CH$_2$)$_4$), 2.53 (s, 3H, CH$_3$), 2.72 (br s, 4H, (CH$_2$)$_2$), 3.65 (s, 2H, CH$_2$), 7.10-7.21 (m, 2H, Ar), 7.82 (s, 1H, Ar). $^{13}$C NMR (75 MHz, CDCl$_3$): δ=19.4, 26.8, 27.5, 53.8, 59.4, 117.2, 117.3, 118.9, 119.0, 124.4, 127.2, 127.2, 141.1, 145.9, 149.3, 151.1. LCMS (ESI): m/z calculated for $C_{16}H_{21}N_2^{15}N_2O+H^+[M+H^+]$: 289.20; Found: 289.02. HPLC purity: 96.1% (at 254 nm).

Example 12. Synthesis of $^{15}$N-Labelled Compound 17

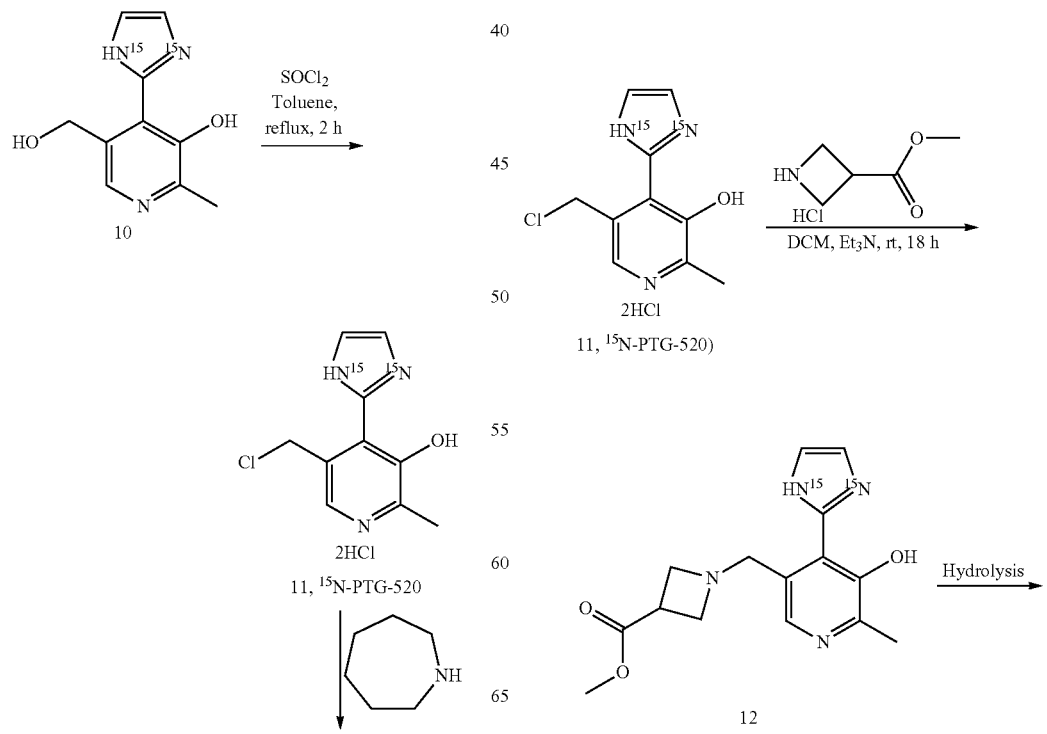

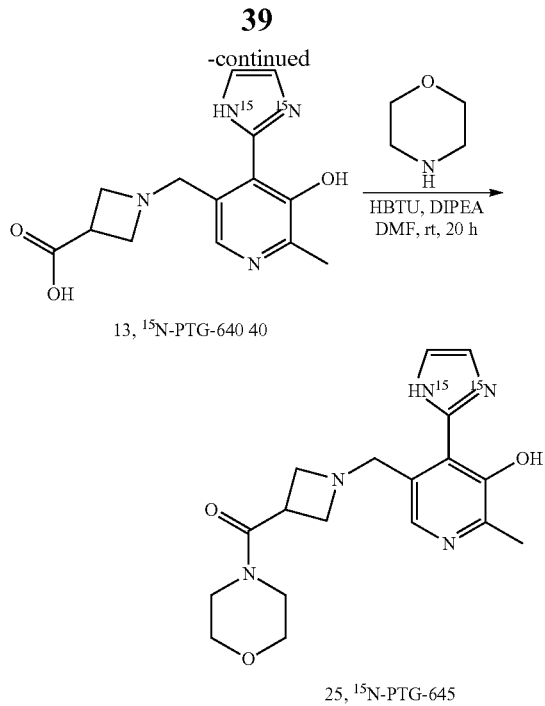

13, ¹⁵N-PTG-640

25, ¹⁵N-PTG-645

To ¹⁵N-labelled chloro-pyridyl imidazole derivative 11 (1 eq.) in methylene chloride were added 3-methyl azetidine carboxylate (1.5 eq.), triethyl amine (8 eq.) and mixture was stirred at room temperature for 20 h. The reaction mixture was concentrated and dissolved in methylene chloride. Organic layer was washed with water, and brine solution and dried over sodium sulphate. Solvent was concentrated, and residue was purified using Combiflash $R_f$ (0-5% of methanol in methylene chloride) and the fractions containing the pure product (TLC) were pooled and evaporated to provide pure product 12 as brown gel; yield: 6.3%; ¹H NMR (300 MHz, CDCl₃): δ=2.52-2.54 (m, 3H, CH₃), 3.29-3.36 (m, 1H, CH), 3.47-3.57 (m, 5H, CH, (CH₂)₂), 3.67-3.77 (m, 5H, CH₃, CH₂), 7.18-7.26 (m, 2H, Ar), 7.88 (s, 1H, Ar).

To 12 (1 eq.) in THF-methanol (1:1) was added 2 N NaOH (2 eq.) solution and mixture was stirred at room temperature for 20 h. The reaction mixture was concentrated and dissolved in water and acidified up to pH 4-5. Mixture was concentrated, and it was used without purification in the next step.

To azetidine carboxylic acid derivative 13 (1 eq.) in DMF (20 vol) were added DIPEA (2 eq.), HBTU (1 eq.) followed by morpholine (1.19 eq) at room temperature and the mixture was stirred at room temperature for 18 h. The reaction mixture was diluted with water (20 vol) and extracted with ethyl acetate (3×25 vol). Organic layer was washed with brine (6 vol) and dried over sodium sulphate. Organic layer was filtered and concentrated. The crude compound was purified using Combiflash $R_f$ (0-10% methanol in DCM) and the fractions containing the pure product (TLC) were pooled and evaporated to provide pure ¹⁵N-labelled amide derivative 25 (SPNC-099, ¹⁵N-labeled PTG-645, 2060-SRT-76-2) as tan solid; yield: 32%; ¹H NMR (300 MHz, CD₃OD): δ=¹H NMR (300 MHz, CDCl₃): δ=2.45 (s, 3H, CH₃), 3.30-3.50 (m, 3H, CH, CH₂), 3.52-3.65 (m, 12H, (CH₂)₆), 3.76 (s, 2H, CH₂), 7.29-7.32 (m, 2H, Ar), 7.89 (s, 1H, Ar). ¹³C NMR (75 MHz, CDCl₃): δ=21.3, 36.0, 46.0, 49.4, 58.5, 62.3, 70.2, 123.2, 126.4, 128.2, 143.4, 148.3, 152.4, 155.2, 175.1. LCMS (ESI): m/z calculated for $C_{18}H_{22}^{15}N_2N_3O_3+H^+[M+H^+]$: 360.14; Found: 360.04. HPLC purity: 99.6% (at 254 nm).

Example 13. Pharmacokinetic Study for PTG-630 and its Salt in Diabetic Rats

The objectives of this study were to perform a single dose injection of PTG-630 followed by blood collection in diabetic rats to assess oral pharmacokinetics parameters. Diabetic Female Sprague Dawley Rat rats were maintained for 4-5 weeks prior the experiment, 2 per cage with free access to dry food and municipal water. Insulin deficient diabetes was induced following an overnight fast by injection of streptozotocin (55 mg/kg ip in 0.9% sterile saline). Hyperglycemia was confirmed 4 days later in a sample of blood obtained by tail prick using a strip operated reflectance meter. Animals were observed daily and weighed weekly during the study period.

Compound 5 (PTG-630 free base) and Compound 19 (PTG-630 HCl salt) solutions were prepared in 0.5% methyl cellulose and 0.1% Tween 20 in water for administration to animals by oral gavage (PO).

Compound 5 was administered at 10 mg/kg and 100 mg/kg. Compound 5 was difficult to dissolve for the 100 mg/kg dose (20 mg/ml solution). The solution was vortexed vigorously for minutes and then sonicated in a water bath for 5 min. The solution remained as a thick creamy yellowish suspension at pH 8. The solution for the 10 mg/kg free base dose (2 mg/ml solution) was easier to prepare. The solution was vortexed for minutes and sonicated for 2 min, few small particles remained (pH 7). The final solution that was administered was a clear, light yellowish solution with few small particulates in suspension.

Compound 19 was administered at 10 mg/kg. Compound 19 was easy to dissolve, with no sonication required. The solution (2 mg/ml) was clear yellowish (although lighter than the Compound 5 solution at 2 mg/ml) with no particulates in suspension. The pH decreased to 3.

After PO administration, blood samples were collected from the tail at 30 min, 1, 2, 4, 6 and 24 h. 3 animals per time points were used with 200-250 μl of blood collected in K₂EDTA tubes from clipped tail. The blood was collected from the 3 same animals at 30 min, 2 and 6 h while it was collected from 3 different animals at 1, 4 and 24 h. Blood samples were centrifuged at 3000 rpm, 4° C. for 30 min, then 100 μl of plasma was collected and stored at −20° C., before shipping for analysis. No adverse effects were observed in diabetic rats over the 24 hours observations, and subsequent weeks.

Example 14. Pharmacokinetic Study for PTG-630

The primary objective of the study was to assess the intravenous (IV) and oral (PO) pharmacokinetics of Compound 5 (PTG-630) its metabolite, Compound 2 (PTG-4997), in plasma, whole blood, kidney, liver, muscle, sciatic nerve, brain, and urine. The samples were analyzed in two batches with standards and QCs prepared on rat plasma and rat urine. Analyst® 1.6 (SCIEX) software was used for statistical analysis of bioanalytical data. Samples were obtained from 15 animals dosed with PTG-630. A total of 33 Plasma, 3 blood samples, 12 kidney samples, 12 liver samples, 12 brain samples, 12 muscle samples, 12 sciatic nerve samples, 6 urine samples were analyzed for PTG-630 and its metabolite PTG-4497.

Study plasma and blood samples were prepared by thawing whole blood and plasma unassisted at room temperature and transferring 20 μL aliquots to a 96 deep well plate for extraction. Dose samples collected at 0.083 h-6 h postdose were diluted 4 times with SD rat plasma prior to plating. Twenty-four (24) hours plasma samples were assayed without dilution. Homogenized tissue samples and urine samples were transferred without additional dilution into a 96 deep well plate in 20 μL aliquots for extraction. Data were summarized by tissue and presented in Table 1 and Table 2. Two sciatic nerve samples were excluded from analysis, due to the insufficient sample size.

TABLE 1

Study Sample Results: Individual Concentration and Mean Summary Statistics for PTG-630 in Plasma and Tissues

| Tissue | Dose Group | Dose (mg/kg) | Animal Number | PTG-630 Concentration, ng/mL Time (hours) postdose | | | | | | |
|---|---|---|---|---|---|---|---|---|---|---|
| | | | | 0.083 | 0.5 | 1 | 2 | 4 | 6 | 24 |
| Kidney | 1(PO) | 100 | 1 | N/A | 1670 | 3220 | 1720 | 1490 | 298 | <BLQ |
| | | | 2 | N/A | 2780 | 4530 | 1290 | 1540 | 634 | <BLQ |
| | | | Mean | | 2225 | 3875 | 1505 | 1515 | 466 | <BLQ |
| | | | SEM | | 555 | 655 | 215 | 25 | 168 | |
| Liver | 1(PO) | 100 | 1 | N/A | 4960 | 7360 | 6270 | 2500 | 397 | <BLQ |
| | | | 2 | N/A | 6470 | 5340 | 3880 | 2330 | 897 | <BLQ |
| | | | Mean | | 5715 | 6350 | 5075 | 2415 | 647 | <BLQ |
| | | | SEM | | 755 | 1010 | 1195 | 85 | 250 | |
| Brain | 1(PO) | 100 | 1 | N/A | 729 | 2290 | 224 | 1380 | 286 | <BLQ |
| | | | 2 | N/A | 2130 | 1690 | 676 | 624 | 202 | <BLQ |
| | | | Mean | | 1430 | 1990 | 450 | 1002 | 244 | <BLQ |
| | | | SEM | | 700.5 | 300 | 226 | 378 | 42 | |
| Sciatic Nerve | 1(PO) | 100 | 1 | N/A | 960 | 1630 | 179* | 1040 | 270* | <BLQ |
| | | | 2 | N/A | 2360 | 2030 | 840 | 937 | 1110 | <BLQ |
| | | | Mean | | 1660 | 1830 | 840 | 989 | 1110 | <BLQ |
| | | | SEM | | 700 | 200 | 0 | 51.5 | 0 | |
| Muscle | 1(PO) | 100 | 1 | N/A | 430 | 1100 | 171 | 507 | <BLQ | <BLQ |
| | | | 2 | N/A | 1120 | 969 | 409 | 295 | 245 | <BLQ |
| | | | Mean | | 775 | 1035 | 290 | 401 | 123 | <BLQ |
| | | | SEM | | 345 | 65.5 | 119 | 106 | 123 | |
| Plasma | 1(PO) | 100 | 1 | N/A | 620 | 1332 | 157.2 | 1096 | 556 | 18.4 |
| | | | 2 | N/A | 1240 | 996 | 390.8 | 492 | 464 | 18.4 |
| | | | Mean | | 930 | 1164 | 274 | 794 | 510 | 18.4 |
| | | | SEM | | 310 | 168 | 117 | 302 | 46 | 0 |
| Plasma | 2(IV) | 5 | 1 | 17480 | 7040 | 3296 | 1836 | 1608 | 648 | 391 |
| | | | 2 | 22080 | 8640 | 5000 | 1944 | 1868 | 2196 | 541 |
| | | | 3 | 21600 | 7960 | 3208 | 1756 | 1120 | 992 | 769 |
| | | | Mean | 20387 | 7880 | 3835 | 1845 | 1532 | 1279 | 567 |
| | | | SEM | 1460 | 464 | 583 | 54.5 | 219 | 469 | 110 |
| Blood | 2(IV) | 5 | 1 | N/A | N/A | N/A | 6080 | N/A | N/A | N/A |
| | | | 2 | N/A | N/A | N/A | 1932 | N/A | N/A | N/A |
| | | | 3 | N/A | N/A | N/A | 1416 | N/A | N/A | N/A |
| | | | Mean | | | | 3143 | | | |
| | | | SEM | | | | 1476 | | | |
| Urine | 2(IV) | 5 | 1 | | | | 1210 | | | 97.4 |
| | | | 2 | | | | 1840 | | | 51.4 |
| | | | 3 | | | | 1560 | | | 257 |
| | | | Mean | | | | 1537 | | | 135 |
| | | | SEM | | | | 182 | | | 62.3 |

*Data is not included in analysis, insufficient sample size

TABLE 2

Study Sample Results: Individual Concentration and Mean Summary Statistics for PTG-4997 in Plasma and Tissues

| Tissue | Dose Group | Dose (mg/kg) | Animal Number | PTG-630 Concentration, ng/mL Time (hours) postdose | | | | | | |
|---|---|---|---|---|---|---|---|---|---|---|
| | | | | 0.083 | 0.5 | 1 | 2 | 4 | 6 | 24 |
| Kidney | 1(PO) | 100 | 1 | N/A | <BLQ | <BLQ | 162 | 145 | 172 | <BLQ |
| | | | 2 | N/A | 173 | <BLQ | <BLQ | 111 | 193 | 212 |
| | | | Mean | | 86.5 | 0 | 81 | 128 | 182.5 | 106 |
| | | | SEM | | 86.5 | 0 | 81 | 17 | 10.5 | 106 |
| Liver | 1(PO) | 100 | 1 | N/A | <BLQ | <BLQ | <BLQ | <BLQ | <BLQ | <BLQ |
| | | | 2 | N/A | <BLQ | <BLQ | <BLQ | <BLQ | <BLQ | <BLQ |
| | | | Mean | | <BLQ | <BLQ | <BLQ | <BLQ | <BLQ | <BLQ |
| | | | SEM | | | | | | | |
| Brain | 1(PO) | 100 | 1 | N/A | <BLQ | <BLQ | <BLQ | <BLQ | <BLQ | <BLQ |
| | | | 2 | N/A | <BLQ | <BLQ | <BLQ | <BLQ | <BLQ | <BLQ |
| | | | Mean | | <BLQ | <BLQ | <BLQ | <BLQ | <BLQ | <BLQ |
| | | | SEM | | | | | | | |

TABLE 2-continued

Study Sample Results: Individual Concentration and Mean Summary Statistics for PTG-4997 in Plasma and Tissues

| Tissue | Group | Dose (mg/kg) | Animal Number | PTG-630 Concentration, ng/mL Time (hours) postdose | | | | | | |
|---|---|---|---|---|---|---|---|---|---|---|
| | | | | 0.083 | 0.5 | 1 | 2 | 4 | 6 | 24 |
| Sciatic Nerve | 1(PO) | 100 | 1 | N/A | <BLQ | <BLQ | <BLQ | <BLQ | <BLQ | <BLQ |
| | | | 2 | N/A | <BLQ | <BLQ | <BLQ | <BLQ | <BLQ | <BLQ |
| | | | Mean | | <BLQ | <BLQ | <BLQ | <BLQ | <BLQ | <BLQ |
| | | | SEM | | | | | | | |
| Muscle | 1(PO) | 100 | 1 | N/A | <BLQ | <BLQ | <BLQ | 108 | 108 | <BLQ |
| | | | 2 | N/A | <BLQ | <BLQ | <BLQ | <BLQ | 147 | <BLQ |
| | | | Mean | | <BLQ | <BLQ | <BLQ | 54 | 127.5 | <BLQ |
| | | | SEM | | | | | 54 | 19.5 | |
| Plasma | 1(PO) | 100 | 1 | N/A | <BLQ | <BLQ | <BLQ | <BLQ | <BLQ | <BLQ |
| | | | 2 | N/A | <BLQ | <BLQ | <BLQ | <BLQ | <BLQ | <BLQ |
| | | | Mean | | <BLQ | <BLQ | <BLQ | <BLQ | <BLQ | <BLQ |
| | | | SEM | | | | | | | |
| Plasma | 2(IV) | 5 | 1 | <BLQ | <BLQ | <BLQ | <BLQ | <BLQ | <BLQ | <BLQ |
| | | | 2 | <BLQ | <BLQ | <BLQ | <BLQ | <BLQ | <BLQ | <BLQ |
| | | | 3 | <BLQ | 135 | <BLQ | <BLQ | <BLQ | <BLQ | <BLQ |
| | | | Mean | <BLQ | 45 | <BLQ | <BLQ | <BLQ | <BLQ | <BLQ |
| | | | SEM | | 45 | | | | | |
| Blood | 2(IV) | 5 | 1 | N/A | | | <BLQ | | | |
| | | | 2 | N/A | | | <BLQ | | | |
| | | | 3 | N/A | | | 121 | | | |
| | | | Mean | | | | 40.3 | | | |
| | | | SEM | | | | 40.3 | | | |
| Urine | 2(IV) | 5 | 1 | | | | 7.70 | | | 7.76 |
| | | | 2 | | | | 44.8 | | | 24.8 |
| | | | 3 | | | | 9.75 | | | 13.3 |
| | | | Mean | | | | 20.8 | | | 15.3 |
| | | | SEM | | | | 12.0 | | | 5.02 |

Further, male Sprague Dawley rats (8-9 weeks old) were treated with Compound 5 (PTG-630). The 12 non-cannulated animals were arbitrarily assigned to groups upon arrival and housed together throughout the experiment. The animals were acclimated to their designated housing for at least 24 hours before the first day of dosing. PTG-630 was formulated in 5% Ethanol and 95% (0.9% Saline for Injection) and administered to the animals by intravenous administration (IV) with blood samples and urine collected at predetermined time points. PTG-630 was formulated in 0.5% methyl cellulose and 0.1% Tween 20 in water for injection and administered to animals by mouth (PO) with blood and tissue samples collected at predetermined time points. Blood samples were collected via cannula from IV dosed rats or by cardiac stick from PO dosed rats at the specified time points for sampling pharmacokinetics.

Blood was collected into $K_2$EDTA tubes. Tubes were mixed gently after blood collection, chilled and centrifuged at 3000 rpm, 4° C. within 30 minutes upon collection. The samples were centrifuged at 4° C. and the resultant plasma separated. Plasma samples were analyzed for concentration of PTG-630 and PTG-4997 using a qualified analytical procedure. Urine from Group 1 was collected via polycarbonate tubes from rats placed in drug metabolism cages. Urine was maintained and room temperature through the collection period. Urine samples were analyzed for concentration of PTG-630 and PTG-4997 using a qualified analytical procedure. Right thigh muscle, liver, brain, right sciatic nerve, and right kidney were collected at the terminal time points for Group 2. Tissues samples were analyzed for concentration of PTG-630 and PTG-4997 using a qualified analytical procedure.

Results: PTG-630 exhibited a substantial exposure in rat plasma with Cmax of 20,400 ng/mL following IV administration. Biphasic decline in exposure with a rapid decrease through 2 hours and a slower decline thereafter through 24 hours after a single IV dose was observed. Significant exposure of PTG-630 (Cmax 567 ng/mL) was remain in plasma 24 hours post IV dose. The calculated terminal phase half-life for IV rout was determined as 15.8 h. Less abundant PTG-630 exposure was determined in rat plasma following PO administration compared to IV route. There was a 17× fold decrease in mean Cmax and 4× fold decrease in AUClast for PO route (Cmax 1160 ng/mL, AUClast 8600 h×ng/mL) over IV route (Cmax20400 ng/mL, AUClast 34000 h×ng/mL). PTG-630 exposure decreased gradually with half-life 3.71 hours. PTG-630 in concentration 18.4 ng/mL was detected in plasma 24 hours post PO dose.

IV administration route associated with 4.25 folds increase in the half-life (15.8 hours) of PTG-630 in plasma in comparison with PO route (3.71 hours). The group Mean Residence Time (MRT) in plasma after a single IV was comparable with those in PO group.

The PO route of administration was <1% bioavailable based on AUCinf for PTG-630. However, based on calculations of the hepatic extraction ratio, it may be possible to increase oral bioavailability with formulation work or it is being transported or metabolized in the gut wall.

PTG-4997 was not detectable in plasma at any timepoint following PO administration and was only detected in the plasma of single animal dosed by IV.

PTG-630 was quantifiable in all tested tissues (liver, kidney, brain, sciatic nerve, muscle). The exposure pattern of PTG-630 in tissues was comparable to those in plasma with Tmax 1 hour. The level of PTG-630 exposure in selected tissues exceed the exposure in plasma up to 3-5 folds. PTG-630 was not detectable in any tissue, except plasma 24 hours postdose. Significant exposure of PTG-630 in brain and sciatic nerve was determined with Cmax 1990 ng/mL for brain and 1830 ng/mL for sciatic nerve, indicating blood brain permeability for compound PTG-630. Half-life of PTG-630 in brain was 4.53 hours, that is 1.3 times higher than in plasma.

The lowest exposure of PTG-630 was detected in muscle with concentration of PTG-630 comparable to those in plasma. The highest exposure of PTG-630 was detected in liver (5.47-folds higher than in plasma, based on Cmax) and in kidney (3.4 folds higher than in plasma, based on Cmax). Analyte primary metabolite PTG-4997 was present in steady level for 24 hours in kidney but remained undetectable in liver samples at any timepoint through 24 hours postdose. Analyte primary metabolite PTG-4997 was also intermittently present in muscle samples 4-6 hours postdose.

PTG-630 was rapidly absorbed in tissues without delay, with Tmax 1 h comparable with plasma Tmax value. Maximum exposure, based on Cmax and AUClast values, was observed in liver with AUC last 2.6 folds higher than in plasma. The lowest exposure in tissues was observed in muscle with PK parameters comparable to plasma. Elimination phase half-life (t1/2) varied in tissues with highest half-life observed in brain (4.53 hours) and the lowest in liver (1.35 hours). PTG-4997 was detected mostly in kidneys with Tmax at 6 hours and half-life 2.36 hours and MRT 11.6 hours. Cmax for PTG-4497 in kidney was 21 times lower and AUC last 3 times lower than PTG-630 in kidneys.

Clearance (CLr) that represents the rate at which a drug is removed from systemic circulation indicate that only 0.09% of PTG-630 per kg of weight was excreted with urine for 24-hour post IV dose. Excretion of PTG-4997 was observed at the rate 34 times lower than PTG-630. An average of 146 ng of PTG-4997 was recovered from each animal for 24 hours incubation period.

The low amounts of PTG-630 and PTG-4997 excreted with urine, lack of hepatic metabolism resulting in PTG 4997 formation in plasma and liver suggest the possibility of a different metabolic product for PTG-630 other than PTG-4997.

Example 15. CYP Inhibition Screening

Compound 5 (PTG-630 free base) and 7 additional compounds for CYP3A P450 inhibition. PTG-630 was also tested for inhibition of 6 other CYP enzymes.

Imidazole (and benzimidazole) containing drugs are ubiquitous in pharmacological practice; however, drug-drug interactions (DDI) have been observed with some imidazole-containing classes, such as the antifungal azoles typified by ketoconazole. It is believed that the imidazole moiety accounts for their ability to inhibit CYP3A, the major DDI enzyme that metabolizes up to 50% of common drugs. The compounds of the disclosure incorporate an imidazole moiety attached to a pyridine ring via the imidazole C-2. They all share an imidazo-hydroxypyridine theme that can bind redox metal ions, while differing in the nature of the X side-chain. The potential of the compounds of the disclosure for DDI was evaluated by screening their inhibition of CYP3A.

Two studies were conducted in human liver microsomes (HLM). Lead candidate PTG-630 was tested using the Eurofins G232 panel (Drug Metab Dispos. 2001 January; 29(1):23-9), where inhibition was measured against seven CYP enzymes; CYP3A4 was tested using two different substrates, midazolam and testosterone. In a second study, inhibition of CYP3A4 (midazolam substrate only) was compared for 8 compounds of interest. The test protocol involved one-point measurements in duplicate, where inhibition was measured at a fixed 10 µM concentration of candidate inhibitors. In all cases, the substrate for each CYP enzyme was at a concentration equal to its specific Km value that was independently obtained from an 8-point dose-response study. Based on the observed value for percent inhibition for each test compound, we calculated of an $IC_{50}$ assuming a competitive mode of inhibition. If percent inhibition for an inhibitor at a concentration of [I] is denoted by P, then:

$$IC_{50} = [I]*(100-P)/P$$

In the single-point assay, [I] is 10 µM. If measured inhibition is 10%, then $IC_{50}=10*(100-10)/10=90$ µM. For 20% inhibition, $IC_{50}=10*(100-20)/20=40$ µM, etc. As discussed in Lin et al. (J Pharm Sci. 2007 September; 96(9):2485-93; doi: 10.1002/jps.20884), CYP inhibition is broadly interpreted as being "potent" if $IC_{50}<1$ µM, "moderate" if $1$ µM$<IC_{50}<10$ µM, and "weak" if $IC_{50}>10$ µM.

The following percent inhibition values were obtained, from which $IC_{50}$ was estimated using the equation above.

| P450 Enzyme, Substrate Utilized | Compound | Inhib Conc. (M) | P % inhib | Estimated $IC_{50}$ (µM) |
|---|---|---|---|---|
| CYP1A inhibition (HLM) phenacetin | PTG-630 | 1.0E−05 | 16.1 | 52.1 |
| CYP2B6 inhibition (HLM), bupropion | PTG-630 | 1.0E−05 | 4.5 | 213 |
| CYP2C19 inhibition (HLM), omeprazole | PTG-630 | 1.0E−05 | 27.5 | 26.4 |
| CYP2C8 inhibition (HLM), amodiaquine | PTG-630 | 1.0E−05 | 21.3 | 37.0 |
| CYP2C9 inhibition (HLM), diclofenac | PTG-630 | 1.0E−05 | 3.4 | 284 |
| CYP2D6 inhibition (HLM), dextromethorphan | PTG-630 | 1.0E−05 | −0.83 | — None |
| CYP3A inhibition (HLM) midazolam | PTG-4997 | 1.0E−05 | −4.9 | — None |
| CYP3A inhibition (HLM) midazolam | PTG-605 | 1.0E−05 | −13.6 | — None |
| CYP3A inhibition (HLM) midazolam | PTG-630 | 1.0E−05 | −12.1 | — None |
| CYP3A inhibition (HLM) midazolam | PTG-640 | 1.0E−05 | −5.6 | — None |
| CYP3A inhibition (HLM) midazolam | PTG-644 | 1.0E−05 | −16.0 | — None |
| CYP3A inhibition (HLM) midazolam | PTG-645 | 1.0E−05 | −9.0 | — None |
| CYP3A inhibition (HLM) midazolam | PTG-647 | 1.0E−05 | −6.6 | — None |
| CYP3A inhibition (HLM) midazolam | PTG-670 | 1.0E−05 | −1.1 | — None |
| CYP3A inhibition (HLM) testosterone | PTG-630 | 1.0E−05 | 1.56 | 631 |

PTG-630 CYP inhibition ranged from weak to undetectable. When 8 different compounds were tested against CYP3A, the major DDI CYP, none showed any inhibitory activity using midazolam as substrate. Further, for PTG-630 CYP3A inhibition using testosterone as substrate showed very weak inhibition. Without being bound by a theory, it is believed that there is no significant concern about the tested compounds being involved in a clinically relevant DDI mediated through inhibition of CYP3A.

It is understood that the examples and embodiments described herein are for illustrative purposes only and that various modifications or changes in light thereof are suggested to persons skilled in the art and are to be incorporated within the spirit and purview of this application and scope of the appended claims. All publications, patents, and patent applications cited herein are hereby incorporated herein by reference for all purposes.

The invention claimed is:
1. A compound of the formula,

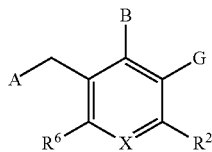

or a pharmaceutically acceptable salt thereof, wherein
X is N, N—O or $CR^1$;
G is —OH, —SH, —$NH_2$, or —$N(R^G)_2$, wherein $R^G$ is hydrogen, ($C_1$-$C_6$)alkyl or —C(O)($C_1$-$C_6$)alkyl;
A is

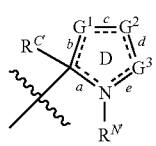

wherein n is 0, 1, 2 or 3;
$R^4$ is ($C_1$-$C_6$)alkyl, halogen, —$OR^{41}$, —$N(R^{41})_2$, —$SR^{41}$, —$S(O)R^{41}$, —$S(O)_2R^{41}$, —$COOR^{41}$, —$CON(R^{41})_2$ or —($C_1$-$C_6$)alkyl-$OR^{41}$,
wherein $R^{41}$ is hydrogen, ($C_1$-$C_6$)alkyl or —C(O)($C_1$-$C_6$)alkyl, or two $R^{41}$ together with N-atom to which they are attached form a morpholinyl;
B is of the formula,

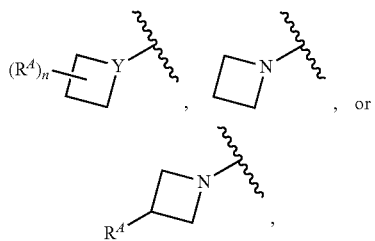

wherein
ring D is (i) monocyclic, and
(ii) unsaturated or aromatic;
$R^{C'}$ is hydrogen;
$G^1$ is O, S, N or $NR^{N'}$;
$G^2$ and $G^3$ each are independently N, O, $CR^3$, $C(R^3)_2$ or $NR^{N'}$, wherein each $R^3$ is independently -$Z^3$-M-$Z^4$-$R^Z$, or two $R^3$ taken together are oxo, wherein
M is —C(O)—, —C(S)—, —S(O)—, —S(O)$_2$—, or absent,
$Z^3$ and $Z^4$ are independently —O—, —S—, —N($R^{N3}$)— or absent, wherein
$R^{N3}$ is hydrogen, ($C_1$-$C_6$)alkyl, ($C_2$-$C_6$)alkenyl, ($C_1$-$C_6$)alkynyl, ($C_1$-$C_6$)haloalkyl, ($C_1$-$C_6$)alkanoyl, ($C_3$-$C_8$)cycloalkanoyl, heterocycloyl, aroyl, heteroaroyl, ($C_1$-$C_6$)alkoxycarbonyl or aryl($C_1$-$C_6$)alkoxycarbonyl, wherein
$R^{N3}$ is optionally substituted with one or more groups which are independently halogen, —OH, amino, ($C_1$-$C_6$)alkylamino, ($C_1$-$C_6$)dialkylamino, —$NO_2$, —CN, ($C_1$-$C_6$)alkyl, aryl, heterocyclyl, heteroaryl, ($C_3$-$C_8$)cycloalkyl, ($C_1$-$C_6$)haloalkyl, ($C_1$-$C_6$)alkoxy, ($C_1$-$C_6$)alkanoyl or aroyl;
$R^Z$ is —H, —($C_1$-$C_6$)alkyl, —($C_2$-$C_6$)alkenyl, —($C_1$-$C_6$)alkynyl, —($C_1$-$C_6$)haloalkyl, —($C_3$-$C_8$)cycloalkyl, —($C_1$-$C_6$)alkylaryl, -heterocycle, -aryl, or -heteroaryl, wherein
$R^Z$ is optionally substituted with at least one $R^{Z'}$, wherein
each $R^{Z'}$ is independently -halogen, —OR, —($C_1$-$C_6$)alkoxy, —C(O)OR, —C(O)R, —C(O)$NR_2$, —S(O)$_2$R, —OS(O)$_2$R, -cyano, -nitro, —($C_1$-$C_6$)alkyl, —($C_1$-$C_6$)haloalkyl, —($C_3$-$C_8$)cycloalkyl, -heterocycloalkyl, or heteroaryl,
provided when M is —S(O)—, —S(O)$_2$— or absent, at least one of $Z^3$ and $Z^4$ is also absent;
$R^{N'}$ is hydrogen or optionally substituted ($C_1$-$C_6$)alkyl;
bonds a, b, c, d, and e are independently a single or double bond,
provided that
(i) no two consecutive atoms in ring D are both oxygen;
(ii) no two consecutive bonds are both double bonds;
(iii) if a or b is a double bond, then $R^{C'}$ is absent; and
(iv) if a or e is a double bond, then $R^{N'}$ is absent;
(v) if b or c is a double bond, then $G^1$ is not O or S;
(vi) if c or d is a double bond, then $G^2$ is not O;
(vii) if d or e is a double bond, then $G^3$ is not O;
$R^1$, $R^2$, and $R^6$ are independently hydrogen, halogen, —$NO_2$, —CN or $R^{Z6}$ wherein
$R^{Z6}$ is ($C_1$-$C_6$)alkyl, ($C_1$-$C_6$)haloalkyl, ($C_3$-$C_8$)cycloalkyl, ($C_1$-$C_6$)alkylaryl, heterocyclyl, aryl or heteroaryl, wherein $R^{Z6}$ is optionally substituted with at least one $R^{Z6'}$,
wherein each $R^{Z6'}$ is independently halogen, —OR, —C(O)OR, —C(O)R, ($C_1$-$C_6$)alkyl or ($C_1$-$C_6$)haloalkyl, wherein each R is independently hydrogen, ($C_1$-$C_6$)alkyl or ($C_1$-$C_6$)haloalkyl,
provided that
when X is $CR^1$
(i) $R^2$, and $R^6$ are not phenyl;
(ii) $R^{Z6}$ is not aryl, heteroaryl, heterocyclyl or ($C_2$-$C_6$)alkenyl,
(iii) when $G^1$ is N, then $G_2$ is not O; and
(iv) two $R^{Z6}$ together may not form oxo; and
when X is N, and
(i) $G^1$ is N, $G^3$ is $CR^3$ and $G^2$ is N, and bonds b and d are each a double bond, all simultaneously; or
(ii) $G^1$ is N, $G^3$ is C(O), $G^2$ is $NR^{N'}$, and bond b is a double bond, all simultaneously;

then either R² or R⁶ is not —NH-aryl or —NH-heteroaryl.

2. The compound according to claim 1, wherein:
X is N;
G is —OH;
B is aromatic; and
G¹ is O, S, N or NR^{N'}; and
G² and G³ are each independently O, N or CR³.

3. The compound according to claim 2, wherein B is imidazolyl, oxazolyl, pyrazolyl, pyrrolyl or isoxazolyl wherein each carbon atom is substituted by R³.

4. The compound according to claim 3, wherein G² and G³ are CR³ or (CR³)₂.

5. The compound according to claim 4, wherein
R^{N'} is substituted with one or more groups which are independently halogen, —OR^{N''}, —NR^{N''}₂, —NO₂, —CN, (C₁-C₆)alkyl, aryl, heterocyclyl, heteroaryl, (C₃-C₈)cycloalkyl or (C₁-C₆)haloalkyl,
wherein each R^{N''} is independently hydrogen, (C₁-C₆) alkyl, (C₁-C₆)haloalkyl, (C₁-C₆)alkoxy, (C₃-C₈)cycloalkyl, heterocycloalkyl, aryl or heteroaryl.

6. The compound according to claim 1, wherein R^A is (C₁-C₆)alkyl, halogen or —(C₁-C₆)alkyl-OR^{A1}, and R^{A1} is hydrogen or (C₁-C₆)alkyl.

7. The compound according to claim 1, wherein R^A is (C₁-C₆)alkyl, halogen, (C₁-C₆)alkyl-OR^{A1}, or —COOR^{A1}, and R^{A1} is hydrogen or (C₁-C₆)alkyl, or two R^{A1} together with N-atom to which they are attached form a morpholinyl.

8. A compound selected from the group consisting of:

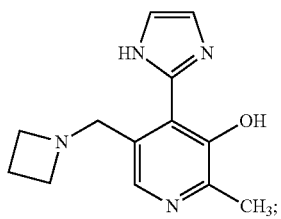

5-(azetidin-1-yl-methyl)-4-(1H-imidazol-2-yl)-2-methylpyridin-3-ol

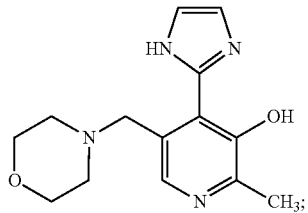

4-(1H-imidazol-2-yl)-2-methyl-5-(morpholinomethyl)pyridin-3-ol

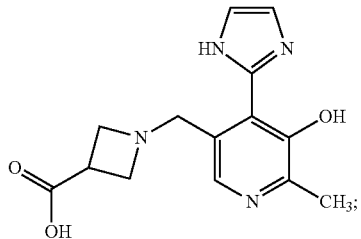

1-((5-hydroxy-4-(1H-imidazol-2-yl)-6-methylpyridin-3-yl)methyl)azetidine-3-carboxylic acid

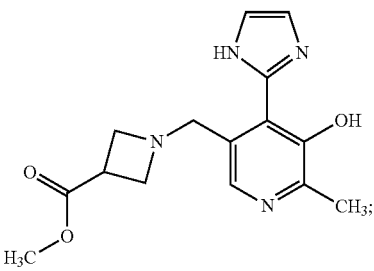

methyl 1-((5-hydroxy-4-(1H-imidazol-2-yl)-6-methylpyridin-3-yl)methyl)azetidine-3-carboxylate

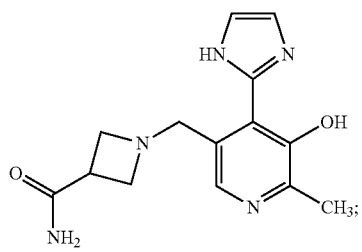

1-((5-hydroxy-4-(1H-imidazol-2-yl)-6-methylpyridin-3-yl)methyl)azetidine-3-carboxamide

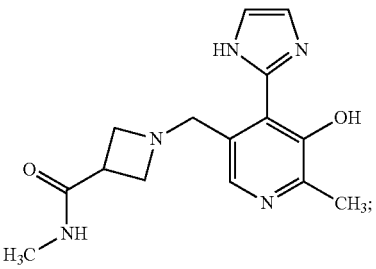

1-((5-hydroxy-4-(1H-imidazol-2-yl)-6-methylpyridin-3-yl)methyl)-N-methylazetidine-3-carboxamide

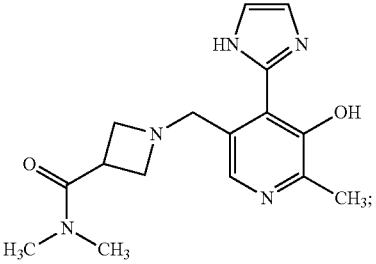

1-((5-hydroxy-4-(1H-imidazol-2-yl)-6-methylpyridin-3-yl)methyl)-N,N-dimethylazetidine-3-carboxamide -continued

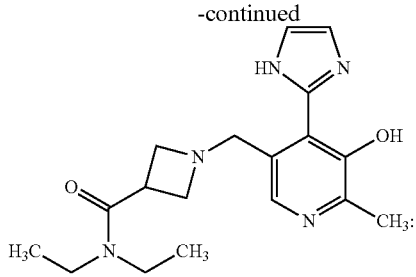

N,N-diethyl-1-((5-hydroxy-4-(1H-imidazol-2-yl)-6-methylpyridin-3-yl)methyl)azetidine-3-carboxamide

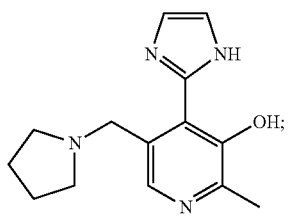

4-(1H-imidazol-2-yl)-2-methyl-5-(pyrrolidin-1-ylmethyl)pyridin-3-ol

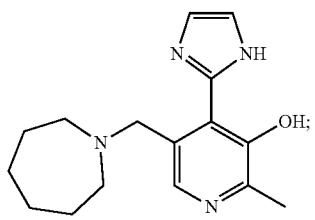

5-(azepan-1-ylmethyl)-4-(1H-imidazol-2-yl)-2-methylpyridin-3-ol

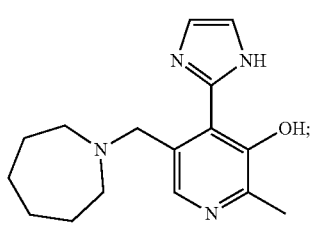

5-(azepan-1-ylmethyl)-4-(1H-imidazol-2-yl)pyridin-3-ol

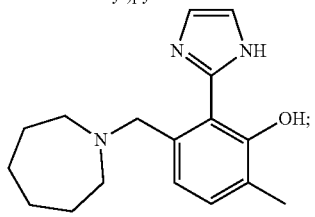

3-(azepan-1-ylmethyl)-2-(1H-imidazol-2-yl)-6-methylphenol

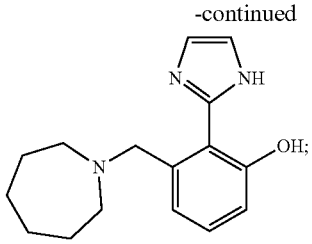

3-(azepan-1-ylmethyl)-2-(1H-imidazol-2-yl)phenol

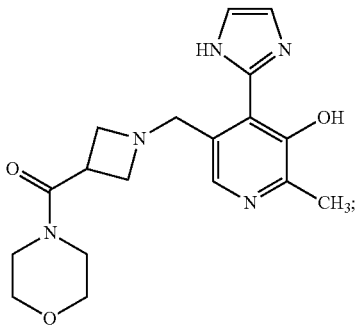

(1-((5-hydroxy-4-(1H-imidazol-2-yl)-6-methylpyridin-3-yl)methyl)azetidin-3-yl)(morpholino)methanone

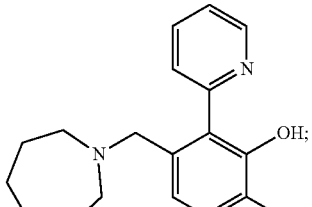

5'-(azepan-1-ylmethyl)-2'-methyl-[2,4'-bipyridin]-3'-ol;

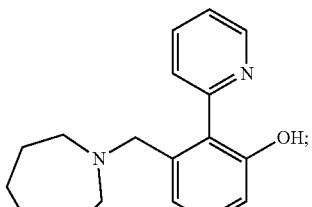

5'-(azepan-1-ylmethyl)-[2,4'-bipyridin]-3'-ol

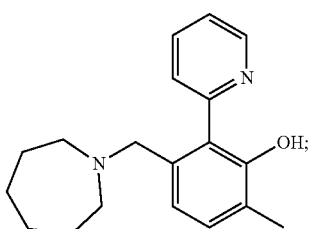

3-(azepan-1-ylmethyl)-6-methyl-2-(pyridin-2-yl)phenol

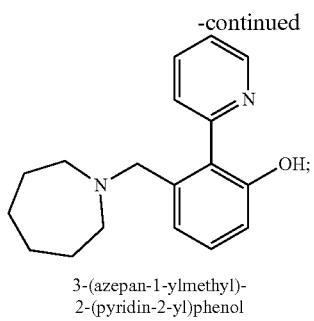

3-(azepan-1-ylmethyl)-
2-(pyridin-2-yl)phenol or a pharmaceutically acceptable salt thereof.

9. The compound of claim 8, wherein the compound is 5-(azepan-1-ylmethyl)-4-(1H-imidazol-2-yl)-2-methylpyridin-3-ol

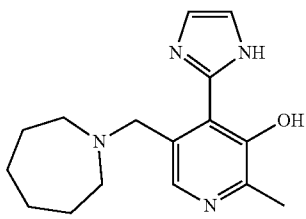 [SMILES: Cc1ncc(CN2CCCCCC2)c(-c2ncc[nH]2)c1O]

or a pharmaceutically acceptable salt thereof.

10. The compound of claim 8, wherein the compound is 4-(1H-imidazol-2-yl)-2-methyl-5-(morpholinomethyl)pyridin-3-ol

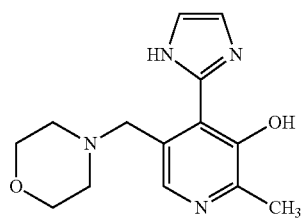 [SMILES: Cc1ncc(CN2CCOCC2)c(-c2ncc[nH]2)c1O]

or a pharmaceutically acceptable salt thereof.

11. The compound according to claim 1, which is in a form of a zinc ($Zn^{2+}$), sodium ($Na^+$), potassium ($K^+$), calcium ($Ca^{2+}$), magnesium ($Mg^{2+}$), or hydrochloride salt.

12. The compound according to claim 11, wherein the compound is complexed with $Zn^{2+}$ in a 1:1, 2:1, or 3:1 stoichiometry.

13. The compound according to claim 8, wherein the pharmaceutically acceptable salt is:
- 4-(1H-imidazol-2-yl)-2-methyl-S-(morpholinomethyl) pyridin-3-ol hydrochloride,
- 4-(1H-imidazol-2-yl)-2-methyl-S-(morpholinomethyl) pyridin-3-ol bishydrochloride,
- 4-(1H-imidazol-2-yl)-2-methyl-S-(morpholinomethyl) pyridin-3-ol trishydrochloride,
- 5-(azepan-1-ylmethyl)-4-(1H-imidazol-2-yl)-2-methylpyridin-3-ol hydrochloride, or
- methyl 1-((5-hydroxy-4-(1H-imidazol-2-yl)-6-methylpyridin-3-yl)methyl)azetidine-3-carboxylate hydrochloride.

14. The compound according to claim 8, which is in a form of a zinc ($Zn^{2+}$), sodium ($Na^+$), potassium ($K^+$), calcium ($Ca^{2+}$), magnesium ($Mg^{2+}$), or hydrochloride salt.

15. The compound according to claim 14, wherein the compound is complexed with $Zn^{2+}$ in a 1:1, 2:1, or 3:1 stoichiometry.

16. A method for treating one or more advanced glycation end product (AGE)- and/or advanced lipoxidation end product (ALE)-associated complications of an AGE- and/or ALE-associated disease in a subject in need thereof comprising administering one or more compounds according to claim 1 to the subject.

17. The method of claim 16 wherein the one or more AGE- and/or ALE-associated complications are selected from the group consisting of accelerated protein aging, retinopathy, nephropathy, proteinuria, impaired glomerular clearance, neuropathy, hyperlipidemia, hypertriglyceridemia, hypercholesterolemia, atherosclerosis, cardiovascular disease, neurodegenerative amyloid diseases, diabetes-associated hyperlipidemia, oxidative modification of proteins, arthritis, connective tissue diseases, amyloidosis, obesity-related complications, proliferation of smooth muscle cells in the aorta, coronary artery disease, and hypertension; and dialysis-related disorders selected from the group consisting of dialysis-related cardiac morbidity and mortality, dialysis-related amyloidosis, dialysis-related increases in permeability of the peritoneal membrane in a dialysis patient, renal failure progression in a dialysis patient, and ultrafiltration failure and peritoneal membrane destruction in a dialysis patient.

18. A method for treating one or more advanced glycation end product (AGE)- and/or advanced lipoxidation end product (ALE)-associated disorders selected from the group consisting of diabetic nephropathy, proteinuria, impaired glomerular clearance, retinopathy, neuropathy, atherosclerosis, diabetes-associated hyperlipidemia, oxidative modification of proteins, arthritis, connective tissue diseases, amyloidosis, obesity-related complications, proliferation of smooth muscle cells in the aorta, coronary artery disease, and hypertension; and dialysis-related disorders selected from the group of dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient, wherein the method comprises administering an effective amount of a one or more compounds according to claim 1 to a subject in need of such treatment.

19. A method for treating one or more advanced glycation end product (AGE)- and/or advanced lipoxidation end product (ALE)-associated complications of an AGE- and/or ALE-associated disease in a subject in need thereof comprising administering one or more compounds according to claim 8 to the subject.

20. The method of claim 19, wherein the one or more AGE- and/or ALE-associated complications are selected from the group consisting of accelerated protein aging, retinopathy, nephropathy, proteinuria, impaired glomerular clearance, neuropathy, hyperlipidemia, hypertriglyceridemia, hypercholesterolemia, atherosclerosis, cardiovascular disease, neurodegenerative amyloid diseases, diabetes-associated hyperlipidemia, oxidative modification of proteins, arthritis, connective tissue diseases, amyloidosis, obesity-related complications, proliferation of smooth muscle cells in the aorta, coronary artery disease, and hypertension; and dialysis-related disorders selected from the group consisting of dialysis-related cardiac morbidity and mortality, dialysis-related amyloidosis, dialysis-related increases in permeability of the peritoneal membrane in a dialysis patient, renal failure progression in a dialysis patient, and ultrafiltration failure and peritoneal membrane destruction in a dialysis patient.

21. A method for treating one or more advanced glycation end product (AGE)- and/or advanced lipoxidation end product (ALE)-associated disorders selected from the group consisting of diabetic nephropathy, proteinuria, impaired glomerular clearance, retinopathy, neuropathy, atherosclerosis, diabetes-associated hyperlipidemia, oxidative modification of proteins, arthritis, connective tissue diseases, amyloidosis, obesity-related complications, proliferation of smooth muscle cells in the aorta, coronary artery disease, and hypertension; and dialysis-related disorders selected from the group of dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient, wherein the method comprises administering an effective amount of a one or more compounds according to claim 8 to a subject in need of such treatment.

\* \* \* \* \*